(12) United States Patent
Hahn et al.

(10) Patent No.: US 10,870,008 B2
(45) Date of Patent: Dec. 22, 2020

(54) CARDIAC RESYNCHRONIZATION USING FUSION PROMOTION FOR TIMING MANAGEMENT

(71) Applicant: CARDIAC PACEMAKERS, INC., St. Paul, MN (US)

(72) Inventors: Stephen J. Hahn, Shoreview, MN (US); Kenneth M. Stein, Minneapolis, MN (US); Yinghong Yu, Shoreview, MN (US); Scott J. Healy, Maple Grove, MN (US); John Morgan, Houghton (GB)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 424 days.

(21) Appl. No.: 15/684,264

(22) Filed: Aug. 23, 2017

(65) Prior Publication Data

US 2018/0056079 A1 Mar. 1, 2018

Related U.S. Application Data

(60) Provisional application No. 62/378,866, filed on Aug. 24, 2016.

(51) Int. Cl.
*A61N 1/372* (2006.01)
*A61B 5/0452* (2006.01)
(Continued)

(52) U.S. Cl.
CPC ........ *A61N 1/37252* (2013.01); *A61B 5/0456* (2013.01); *A61B 5/04525* (2013.01);
(Continued)

(58) Field of Classification Search
CPC ............ A61N 1/37252; A61N 1/39622; A61N 1/3627; A61N 1/36592; A61N 1/3756;
(Continued)

(56) References Cited

U.S. PATENT DOCUMENTS 3,835,864 A 9/1974 Rasor et al.
3,943,936 A 3/1976 Rasor et al.
(Continued)

FOREIGN PATENT DOCUMENTS

AU 2008279789 B2 10/2011
AU 2008329620 B2 5/2014
(Continued)

OTHER PUBLICATIONS

US 8,886,318 B2, 11/2014, Jacobson et al. (withdrawn)
(Continued)

*Primary Examiner* — Lindsey G Wehrheim
(74) *Attorney, Agent, or Firm* — Seager, Tufte & Wickhem LLP

(57) ABSTRACT

Methods, systems and devices for providing cardiac resynchronization therapy (CRT) to a patient using a leadless cardiac pacemaker and an extracardiac device. The extracardiac device is configured to analyze one or more QRS complexes of the patient's heart, determine whether fusion pacing is taking place, and, if not, to communicate with the leadless cardiac pacemaker to adjust intervals used in the CRT in order to generate desirable fusion of the pace and intrinsic signals. The extracardiac device may take the form of a subcutaneous implantable monitor, a subcutaneous implantable defibrillator, or other devices including wearable devices.

15 Claims, 16 Drawing Sheets

(51) Int. Cl.
*A61B 5/0456* (2006.01)
*A61N 1/365* (2006.01)
*A61N 1/362* (2006.01)
*A61N 1/39* (2006.01)
*A61N 1/375* (2006.01)
*A61N 1/378* (2006.01)
*A61N 1/368* (2006.01)

(52) U.S. Cl.
CPC ....... *A61N 1/3627* (2013.01); *A61N 1/36592* (2013.01); *A61N 1/378* (2013.01); *A61N 1/3756* (2013.01); *A61N 1/3918* (2013.01); *A61N 1/3962* (2013.01); *A61N 1/39622* (2017.08); *A61N 1/3682* (2013.01); *A61N 1/36843* (2017.08); *A61N 1/37288* (2013.01); *A61N 1/37512* (2017.08)

(58) Field of Classification Search
CPC .... A61N 1/378; A61N 1/3918; A61N 1/3962; A61N 1/36843; A61N 1/37512; A61N 1/3682; A61N 1/37288; A61B 5/04525; A61B 5/0456
See application file for complete search history.

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole, Jr. |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,702,427 A | 12/1997 | Ecker et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |

(56) References Cited

U.S. PATENT DOCUMENTS

| | | |
|---|---|---|
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,505,077 B1 | 1/2003 | Kast et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |

(56) References Cited

U.S. PATENT DOCUMENTS

| | | |
|---|---|---|
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,575 B2 | 12/2006 | Ostroff et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,189,204 B2 | 3/2007 | Ni et al. |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,376,458 B2 | 5/2008 | Palreddy et al. |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,477,935 B2 | 1/2009 | Palreddy et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,340 B2 | 8/2010 | Sanghera et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,809,441 B2 | 10/2010 | Kane et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |

(56) References Cited

U.S. PATENT DOCUMENTS

| | | |
|---|---|---|
| 7,946,997 B2 | 5/2011 | Hubinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,079,959 B2 | 12/2011 | Sanghera et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,116,867 B2 | 2/2012 | Ostroff |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,157,813 B2 | 4/2012 | Ko et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,195,308 B2 | 6/2012 | Frank et al. |
| 8,200,341 B2 | 6/2012 | Sanghera et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,034 B2 | 12/2012 | Patangay et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,399 B2 | 7/2013 | Degroot et al. |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,483,843 B2 | 7/2013 | Sanghera et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,878 B2 | 10/2013 | Allavatam et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,626,310 B2 | 1/2014 | Barror et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |

(56) References Cited

U.S. PATENT DOCUMENTS

| | | |
|---|---|---|
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,325 B2 | 11/2014 | Boling et al. |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,072,914 B2 | 7/2015 | Greenhut et al. |
| 9,079,035 B2 | 7/2015 | Sanghera et al. |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishier et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |

(56) References Cited

U.S. PATENT DOCUMENTS

| | | |
|---|---|---|
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0275522 A1 | 11/2008 | Dong et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | Brooke |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0264949 A1 | 10/2009 | Dong et al. |
| 2009/0266573 A1 | 10/2009 | Engmark et al. |
| 2009/0270937 A1 | 10/2009 | Yonce et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |

(56) References Cited

U.S. PATENT DOCUMENTS

| | | |
|---|---|---|
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0305646 A1 | 12/2010 | Schulte |
| 2010/0312309 A1 | 12/2010 | Harding |
| 2010/0331905 A1 | 12/2010 | Li et al. |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0178567 A1 | 7/2011 | Pei et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0029335 A1 | 2/2012 | Sudam et al. |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0030484 A1 | 1/2013 | Zhang et al. |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0245709 A1 | 9/2013 | Bohn et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0310890 A1 | 11/2013 | Sweeney |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |

(56) References Cited

U.S. PATENT DOCUMENTS

| | | |
|---|---|---|
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0163631 A1 | 6/2014 | Maskara et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207013 A1 | 7/2014 | Lian et al. |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222099 A1 | 8/2014 | Sweeney |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0236253 A1 | 8/2014 | Ghosh et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0032173 A1 | 1/2015 | Ghosh |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0142069 A1* | 5/2015 | Sambelashvili ...... A61N 1/3688 607/18 |
| 2015/0142070 A1 | 5/2015 | Sambelashvili |
| 2015/0157861 A1 | 6/2015 | Aghassian |
| 2015/0165199 A1 | 6/2015 | Karst et al. |
| 2015/0173655 A1 | 6/2015 | Demmer et al. |
| 2015/0182751 A1 | 7/2015 | Ghosh et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297902 A1 | 10/2015 | Stahmann et al. |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0360036 A1 | 12/2015 | Kane et al. |
| 2016/0007873 A1 | 1/2016 | Huelskamp et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0038742 A1 | 2/2016 | Stahmann et al. |
| 2016/0045131 A1 | 2/2016 | Siejko |
| 2016/0045132 A1 | 2/2016 | Siejko |
| 2016/0045136 A1 | 2/2016 | Siejko et al. |
| 2016/0059007 A1 | 3/2016 | Koop |
| 2016/0059022 A1 | 3/2016 | Stahmann et al. |
| 2016/0059024 A1 | 3/2016 | Stahmann et al. |
| 2016/0059025 A1 | 3/2016 | Stahmann et al. |
| 2016/0089539 A1 | 3/2016 | Gilkerson et al. |
| 2016/0121127 A1 | 5/2016 | Klimovitch et al. |
| 2016/0121128 A1 | 5/2016 | Fishier et al. |
| 2016/0121129 A1 | 5/2016 | Persson et al. |
| 2016/0144190 A1 | 5/2016 | Cao et al. |
| 2016/0151621 A1 | 6/2016 | Maile et al. |
| 2016/0175601 A1 | 6/2016 | Nabutovsky et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0271406 A1 | 9/2016 | Maile et al. |
| 2016/0277097 A1 | 9/2016 | Ludwig et al. |
| 2016/0296131 A1 | 10/2016 | An et al. |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0021159 A1 | 1/2017 | Reddy et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0056665 A1 | 3/2017 | Kane et al. |
| 2017/0056666 A1 | 3/2017 | Kane et al. |
| 2017/0112399 A1 | 4/2017 | Brisben et al. |
| 2017/0113040 A1 | 4/2017 | Brisben et al. |
| 2017/0113050 A1 | 4/2017 | Brisben et al. |
| 2017/0113053 A1 | 4/2017 | Brisben et al. |
| 2017/0156617 A1 | 6/2017 | Allavatam et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2017/0368360 A1 | 12/2017 | Hahn et al. |
| 2018/0008829 A1 | 1/2018 | An et al. |
| 2018/0008831 A1 | 1/2018 | An et al. |
| 2018/0021567 A1 | 1/2018 | An et al. |
| 2018/0021581 A1 | 1/2018 | An et al. |
| 2018/0021582 A1 | 1/2018 | An et al. |
| 2018/0021584 A1 | 1/2018 | An et al. |
| 2018/0036527 A1 | 2/2018 | Reddy et al. |
| 2018/0056075 A1 | 3/2018 | Hahn et al. |

(56) References Cited

U.S. PATENT DOCUMENTS

| | | |
|---|---|---|
| 2018/0056079 A1 | 3/2018 | Hahn et al. |
| 2018/0078773 A1 | 3/2018 | Thakur et al. |
| 2018/0116593 A1 | 5/2018 | An et al. |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 5/2007 |
| WO | 2007075974 A2 | 7/2007 |
| WO | 2009006531 A1 | 1/2009 |
| WO | 2010088485 A1 | 8/2010 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |
| WO | 2016118735 A1 | 7/2016 |

OTHER PUBLICATIONS

International Search Report and Written Opinion dated Nov. 23, 2017 for International Application No. PCT/US2017/048179.
"Instructions for Use System 1, Leadless Cardiac Pacemaker (LCP) and Delivery Catheter," Nanostim Leadless Pacemakers, pp. 1-28, 2013.
Hachisuka et al., "Development and Performance Analysis of an Intra-Body Communication Device," The 12th International Conference on Solid State Sensors, Actuators and Microsystems, vol. 4A1.3, pp. 1722-1725, 2003.
Spickler et al., "Totally Self-Contained Intracardiac Pacemaker," Journal of Electrocardiology, vol. 3(3&4): 324-331, 1970.
Wegmüller, "Intra-Body Communication for Biomedical Sensor Networks," Diss. ETH, No. 17323, 1-173, 2007.
Seyedi et al., "A Survey on Intrabody Communications for Body Area Network Application," IEEE Transactions on Biomedical Engineering, vol. 60(8): 2067-2079, 2013.

* cited by examiner

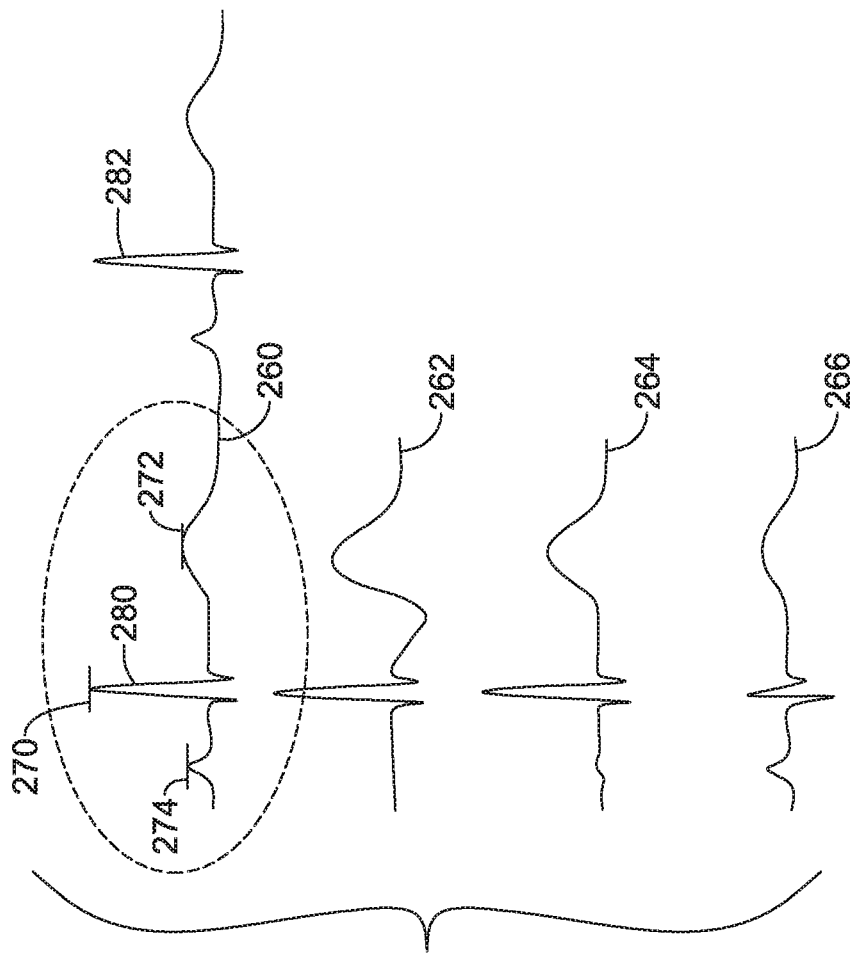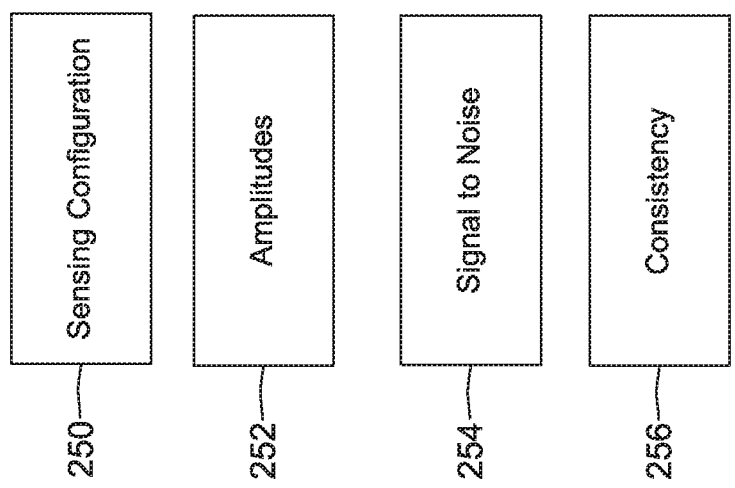
Figure 6

CARDIAC RESYNCHRONIZATION USING FUSION PROMOTION FOR TIMING MANAGEMENT

CROSS REFERENCE TO RELATED APPLICATIONS

The present application claims the benefit of and priority to U.S. Provisional Patent Application Ser. No. 62/378,866, filed Aug. 24, 2016, the disclosure of which is incorporated by reference.

BACKGROUND

Cardiac resynchronization therapy (CRT) modifies the electrical activation and contractions of the heart's chambers to enhance pumping efficiency. Benefits may include increased exercise capacity and reduced hospitalization and mortality. More particularly, CRT devices operate by affecting the timing of contraction of one or more cardiac chambers relative to one or more other cardiac chambers. For example, contractions of one or more of the ventricle(s) may be timed relative to contraction of the atria, or contractions of the left and right ventricles may be timed relative to one another.

A "fusion" beat occurs when multiple activation signals affect the same cardiac tissue at the same time. For example, electrical fusion between pacing of one ventricle with spontaneous activation of another ventricle (for example, paced left ventricular (LV) activation and intrinsic right ventricular (RV) activation) produces a fusion beat. The generation of fusion beats is a goal of CRT in many circumstances.

Prior systems generally include intracardiac electrodes coupled via transvenous leads to an implanted pulse generator. The leads of such systems are widely known as introducing various morbidities and are prone to eventual conductor and/or insulator failure. Such issues likely reduce usage of CRT within the indicated population of heart failure patients.

Such prior lead systems typically include ventricular and atrial components to facilitate sensing of atrial and ventricular events to optimize CRT timing. For example, in some patients, CRT may be achieved by pacing the left ventricle at a specific time relative to detection of an atrial event. The atrial signal may conduct to the right ventricle (RV) via natural conduction to generate an RV contraction, with paced LV contraction occurring at a desirable time relative to the RV contraction to yield a fusion beat. The interval from the atrial sensed event to the LV pace may be adjusted to optimize cardiac response in prior systems.

Newer generation pacemakers include the leadless cardiac pacemaker (LCP), which can be implanted entirely within the heart and does not require a transvenous (or any) lead. Such devices are commercially available on a limited basis, but are currently indicated for and capable of use in only bradycardia pacing. With further enhancements, the LCP also presents an opportunity to provide an alternative to traditional CRT using transvenous leads. New and alternative systems, devices and methods directed at providing CRT using the LCP are desired.

Overview

The present inventors have recognized, among other things, that a problem to be solved is that the absence of an intracardiac lead makes detection of an atrial event for purposes of CRT potentially difficult for a system using one or more ventricular LCP devices. U.S. Provisional Patent Application Ser. No. 62/355,121 suggests certain methods that may use an extracardaic device (such as a subcutaneous cardiac monitor (SCM), a subcutaneous implantable cardiac defibrillator (SICD), or a substernal variant of the SICD) to detect P-waves and provide timing information for use by an LCP. In some patients, however, P-waves may be difficult to detect or highly variable as sensed in the far field by an SCM or SICD, making reliance on P-wave detection possibly difficult.

As an alternative to reliance on atrial event detection, the present invention is directed at a different approach. An LCP is configured to provide pacing therapy at predetermined pace to pace intervals. The morphology (shape) of resulting cardiac electrical signals is monitored by an extracardiac device, such as an SCM or SICD, to determine whether the delivered pacing is resulting in desirable fusion beats. The extracardiac device communicates with the LCP to modify timing of the pace to pace intervals to ensure repeatable fusion.

A first non-limiting example takes the form of a method of providing cardiac resynchronization therapy (CRT) to a patient comprising: in a first device, delivering pacing pulses at predetermined intervals relative to previous pacing pulses; in a second device, monitoring cardiac electrical signals to determine whether pacing therapy is causing: a) one or more fusion beats; b) one or more pace captured beats; or c) one or more intrinsic beats; and selectively communicating from the second device to the first device to adjust the predetermined interval.

Additionally or alternatively, a second non-limiting example takes the form of the first non-limiting example, wherein the step of selectively communicating is performed in order to adjust the predetermined interval such that the pacing pulses cause fusion beats.

Additionally or alternatively, a third non-limiting example takes the form of the first non-limiting example, wherein the step of communicating from the second device to the first device is performed as follows: if b), communicating an extension of the predetermined interval; and if c), communicating a reduction of the predetermined interval.

Additionally or alternatively, a fourth non-limiting example takes the form of the first non-limiting example, wherein the step of monitoring cardiac electrical signals is performed by: obtaining a single cardiac complex following at a pace pulse delivery; and comparing the single cardiac complex to at least one of the following templates: a fusion beat template; a pace captured beat template; and an intrinsic beat template; in order to determine which of a), b), or c) resulted from the pacing pulse.

Additionally or alternatively, a fifth non-limiting example takes the form of the fourth non-limiting example, wherein the step of comparing a portion of the monitored cardiac electrical signals to at least one of the templates is performed using at least one of: a principle components analysis; a wavelet transform analysis; a difference of area comparison; or a correlation waveform analysis.

Additionally or alternatively, a sixth non-limiting example takes the form of the first non-limiting example, wherein the step of monitoring cardiac electrical signals is performed by: capturing a plurality QRS complexes and averaging signals therefrom to generate a composite cardiac complex; and comparing the composite cardiac complex to at least one of a plurality of templates including at least: a fusion beat template; a pace captured beat template; and an intrinsic beat template; in order to determine which of a), b), or c) resulted from a set of pacing pulses.

Additionally or alternatively, a seventh non-limiting example takes the form of the sixth non-limiting example, wherein the step of comparing a portion of the monitored cardiac electrical signals to at least one of the templates is performed using at least one of: a principle components analysis; a wavelet transform analysis; a difference of area comparison; or a correlation waveform analysis.

Additionally or alternatively, an eighth non-limiting example takes the form of the first non-limiting example, wherein the step of monitoring cardiac signals is performed by extracting one or more shape features from one or more QRS complexes, the shape features comprising one or more amplitudes or widths.

Additionally or alternatively, a ninth non-limiting example takes the form of the first non-limiting example, wherein, if c), the second device is further configured to compare a time at which the pacing pulse is delivered relative to the time of the intrinsic beat in order to determine whether: the pacing pulse was delivered too late to capture the heart of the patient and, if so, the step of selectively communicating from the second device is performed to reduce the predetermined interval; or the pacing pulse was delivered at a time which likely would capture the heart and, if so, the step of selectively communicating from the second device is performed to indicate an increase in at least one of pacing pulse amplitude or pacing pulse width.

Additionally or alternatively, a tenth non-limiting example takes the form of the first non-limiting example, wherein the step of selectively communicating is performed after each detected cardiac beat.

Additionally or alternatively, an eleventh non-limiting example takes the form of the first non-limiting example, wherein the step of selectively communicating is performed as follows: if a), communication is performed at an interval; or if b) or c), communication is performed to adjust the pacing parameters after each determination that b) or c) is taking place.

Additionally or alternatively, a twelfth non-limiting example takes the form of the first non-limiting example, wherein neither the first device nor the second device detects an atrial event in order to provide the CRT.

A thirteenth non-limiting example takes the form of a method of providing cardiac resynchronization therapy (CRT) to a patient comprising: in a first device, delivering pacing pulses using a first configuration calling for predetermined intervals relative to previous pacing pulses; in a second device, monitoring cardiac electrical signals to determine whether pacing therapy is causing one or more fusion beats; and: if the pacing therapy is causing one or more fusion beats, the second device preserving the first configuration of the first device; or if the pacing therapy is not causing one or more fusion beats, the second device communicating to the first device to change the first configuration.

Additionally or alternatively, a fourteenth non-limiting example takes the form of the thirteenth non-limiting example, further comprising second device determining how to change the first configuration by: determining that the pacing therapy is causing pace captured beats to take place; and determining that the predetermined intervals should be longer; wherein the step of the second device communicating to the first device to change the first configuration includes communicating that the predetermined intervals should be longer.

Additionally or alternatively, a fifteenth non-limiting example takes the form of the fourteenth non-limiting example, in which the second device is configured to determine that the pacing therapy is causing pace captured beats to take place by: sensing a QRS complex associated with a pacing therapy delivery; comparing the QRS complex to at least a first template associated with a fusion beat and a second template associated with a pace captured beat; and determining that the QRS complex better resembles the second template than the first template.

Additionally or alternatively, a sixteenth non-limiting example takes the form of the thirteenth non-limiting example, further comprising second device determining how to change the first configuration by: determining that the pacing therapy is allowing intrinsic beats to occur; and determining that the predetermined intervals should be longer.

Additionally or alternatively, a seventeenth non-limiting example takes the form of the sixteenth non-limiting example, in which the second device is configured to determine that the pacing therapy is allowing intrinsic beats to occur by: sensing a QRS complex associated with a pacing therapy delivery; comparing the QRS complex to at least a first template associated with a fusion beat and a second template associated with an intrinsic beat; and determining that the QRS complex better resembles the second template than the first template.

Additionally or alternatively, an eighteenth non-limiting example takes the form of the sixteenth non-limiting example, further comprising the second device also determining that one or more characteristics of a pace waveform should be modified to improve a likelihood that delivered therapy will enhance cardiac contraction by at least one of increasing a pace therapy pulse width or increasing a pace therapy amplitude.

A nineteenth non-limiting example takes the form of an implantable medical device (IMD) configured for use as part of a cardiac therapy system comprising a leadless cardiac pacemaker (LCP) and the IMD, the IMD comprising: a plurality of electrodes for sensing cardiac activity; and operational circuitry configured to receive signals from the plurality of electrodes and analyze cardiac activity as follows: sense a QRS complex; analyze the QRS complex to determine whether the QRS complex represents a fusion beat; wherein the operational circuitry is further configured to communicate to the LCP that a pacing interval change is needed to attain fusion if the QRS complex does not represent a fusion beat.

Additionally or alternatively, a twentieth non-limiting example takes the form of the nineteenth non-limiting example, wherein the operational circuitry is configured to determine whether the pacing interval change is an increase or decrease in the pacing interval.

Additionally or alternatively, a twenty-first non-limiting example takes the form of the twentieth non-limiting example, wherein the operational circuitry is configured to analyze the QRS complex to determine whether the QRS complex represents a left ventricular (LV) paced beat or an intrinsic beat and to determine whether the pacing interval change is an increase or decrease as follows: if the QRS complex represents an LV paced beat, determining that the pacing interval change is an increase in the pacing interval; or if the QRS complex represents an intrinsic beat, determining that the pacing interval change is a decrease in the pacing interval.

Additionally or alternatively, a twenty-second non-limiting example takes the form of the nineteenth non-limiting example, wherein the operational circuitry is configured to analyze the QRS complex to determine whether the QRS complex represents a left ventricular (LV) paced beat and to determine whether the pacing interval change is an increase or decrease as follows: if the QRS complex represents an LV paced beat, determining that the pacing interval change is an increase in the pacing interval; or otherwise determining that the pacing interval change is a decrease in the pacing interval.

Additionally or alternatively, a twenty-third non-limiting example takes the form of the nineteenth non-limiting example, wherein the operational circuitry is configured to analyze the QRS complex to determine whether the QRS complex represents an intrinsic beat and is configured to determine whether the pacing interval change is an increase or decrease as follows: if the QRS complex resembles an intrinsic beat, determining that the pacing interval change is a decrease in the pacing interval; or otherwise determining that the pacing interval change is an increase in the pacing interval.

Additionally or alternatively, a twenty-fourth non-limiting example takes the form of the nineteenth non-limiting example, wherein the operational circuitry is configured to identify delivery of a pacing stimulus by the LCP and to analyze the QRS complex in response to identifying delivery of a pacing stimulus by the LCP.

Additionally or alternatively, a twenty-fifth non-limiting example takes the form of the nineteenth non-limiting example, wherein the operational circuitry is configured to receive a communication from an LCP indicating delivery of a pacing stimulus by the LCP and to analyze the QRS complex in response receiving the communication.

Additionally or alternatively, a twenty-sixth non-limiting example takes the form of the nineteenth non-limiting example, wherein the operational circuitry is configured to analyze the QRS complex to determine whether the QRS complex represents a fusion beat by comparing the QRS complex to a template for a fusion beat.

Additionally or alternatively, a twenty-seventh non-limiting example takes the form of the nineteenth non-limiting example, wherein the operational circuitry is configured to analyze the QRS complex to determine whether the QRS complex represents a fusion beat by comparing the QRS complex to a plurality of templates including at least one template which represents a fusion beat and at least one template which does not represent a fusion beat.

Additionally or alternatively, a twenty-eighth non-limiting example takes the form of the an 1 MB as in either of the twenty-sixth or twenty-seventh non-limiting examples, wherein the operational circuitry is configured to perform comparisons to a template using one of difference of area analysis, principal components analysis, wavelet transform analysis, or correlation waveform analysis.

Additionally or alternatively, a twenty-ninth non-limiting example takes the form of the nineteenth non-limiting example, wherein the operational circuitry is configured to use a combination of signal features to analyze the QRS complex to determine whether the QRS complex represents a fusion beat, including at least QRS width.

Additionally or alternatively, a thirtieth non-limiting example takes the form of an IMD as in any of the twenty-sixth, twenty-seventh, or twenty-ninth non-limiting examples, wherein the operational circuitry is configured to analyze the QRS complex to determine whether the QRS complex represents a fusion beat by including the QRS complex among a composite cardiac signal encompassing a plurality of QRS complexes.

Additionally or alternatively, a thirty-first non-limiting example takes the form of the thirtieth non-limiting example, wherein the operational circuitry is configured to calculate a composite signal for a plurality of QRS complexes and only analyzes whether the QRS complex represents a fusion beat at intervals of at least two one cardiac cycles.

Additionally or alternatively, a thirty-second non-limiting example takes the form of the nineteenth non-limiting example, wherein the operational circuitry is configured to recall whether a preceding QRS complex represented a fusion beat and: if so, to analyze the QRS complex to determine whether the QRS complex represents a fusion beat by comparing the QRS complex to the preceding QRS complex and if the QRS complex matches the preceding QRS complex, to determine that the QRS complex represents a fusion beat and otherwise to determine that the QRS complex does not represent a fusion beat; or if not, to analyze the QRS complex by comparing it to at least one stored template including a template that represents a fusion beat.

Additionally or alternatively, a thirty-third non-limiting example takes the form of the nineteenth non-limiting example, wherein the operational circuitry is configured to recall whether a preceding QRS complex represented a fusion beat and: if so, to analyze the QRS complex to determine whether the QRS complex represents a fusion beat by comparing the QRS complex to the preceding QRS complex and if the QRS complex matches the preceding QRS complex, to determine that the QRS complex represents a fusion beat and otherwise to determine that the QRS complex does not represent a fusion beat; or if not, to analyze the QRS complex by reviewing one or more rules including at least a first rule related to width and a second rule related to polarity.

Additionally or alternatively, a thirty-fourth non-limiting example takes the form of system comprising an IMD as in any of the nineteenth to thirty-third non-limiting examples, and an LCP, wherein the LCP is configured to receive a communication from the IMD indicating that a pacing interval change is needed to attain fusion and, in response to the communication, to make a change to a pace to pace interval.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 6 illustrates selected factors for sensing configuration;

DETAILED DESCRIPTION

The following description should be read with reference to the drawings. The description and the drawings, which are not necessarily to scale, depict illustrative embodiments and are not intended to limit the scope of the disclosure.

Figure 1:
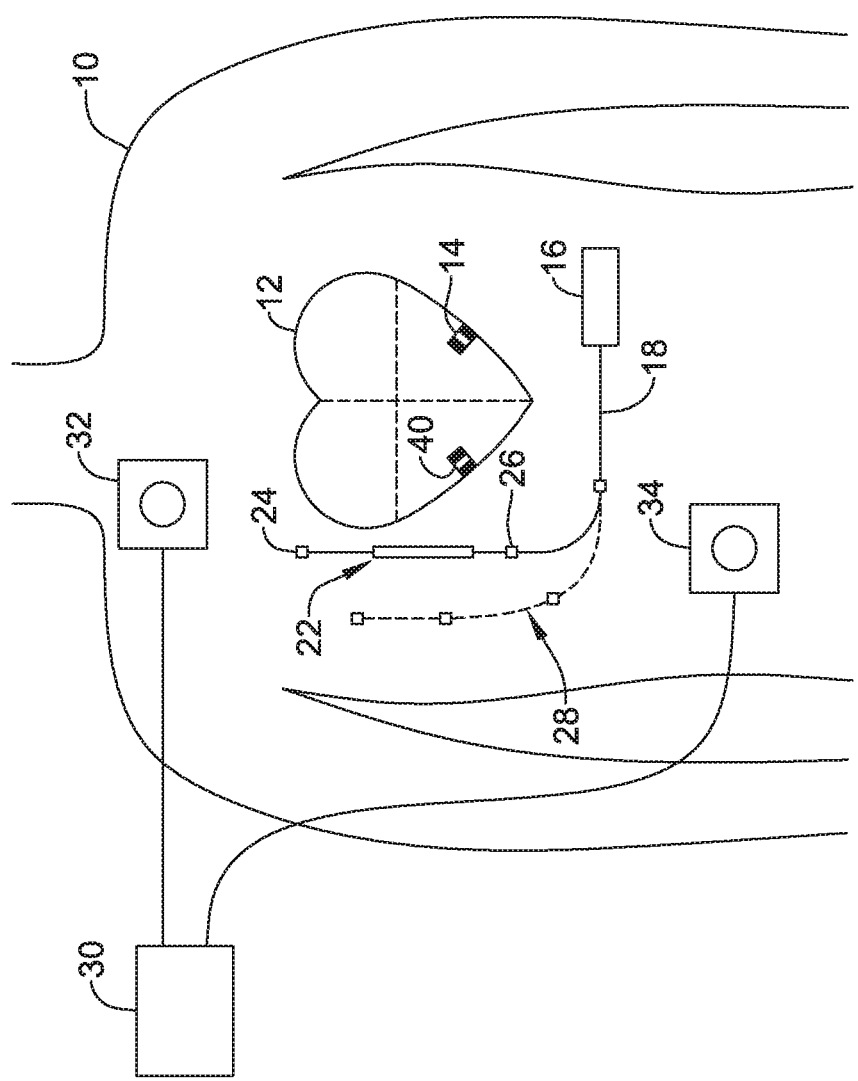
FIG. 1 illustrates a patient having a plurality of implantable medical devices.

FIG. 1 illustrates a patient 10 with a first implanted medical device, shown as a leadless cardiac pacemaker (LCP) 14 implanted inside the heart 12, in the left ventricle for illustrative purposes. The LCP 14 may be implanted in other chambers, such as the right ventricle or in the atrium, and more than one LCP may be provided.

A second medical device in the form of a subcutaneous implantable defibrillator (SICD) having a left axillary canister 16 and a lead 18 is also present. The illustrative lead 18 is shown with a defibrillation coil 22 and sensing electrodes 24, 26 distal and proximal of the coil 22. The lead 18 may optionally include a bifurcation 28 to provide an additional set of sensing or stimulus providing electrodes, if desired.

In some embodiments the lead may be as shown, for example, in U.S. Pat. No. 9,079,035, titled ELECTRODE SPACING IN A SUBCUTANEOUS IMPLANTABLE CARDIAC STIMULUS DEVICE, the disclosure of which is incorporated herein by reference. Rather than bifurcation, plural leads may be provided as shown, for example, in U.S. Pat. No. 7,149,575, titled SUBCUTANEOUS CARDIAC STIMULATOR DEVICE HAVING AN ANTERIORLY POSITIONED ELECTRODE. Any suitable design for single, multiple, or bifurcated implantable leads may be used.

The lead 18 may be implanted entirely subcutaneously, such as by extending across the anterior or posterior of the chest, or by going partly across the chest in a lateral/medial direction and then superiorly toward the head along the sternum. Some examples and discussion of subcutaneous lead implantation may be found in U.S. Pat. No. 8,157,813, titled APPARATUS AND METHOD FOR SUBCUTANEOUS ELECTRODE INSERTION, and US PG Publication No. 20120029335, titled SUBCUTANEOUS LEADS AND METHODS OF IMPLANT AND EXPLANT, the disclosures of which are incorporated herein by reference. Additional subcutaneous placements are discussed in U.S. Pat. No. 6,721,597, titled SUBCUTANEOUS ONLY IMPLANTABLE CARDIOVERTER DEFIBRILLATOR AND OPTIONAL PACER, and the above mentioned U.S. Pat. No. 7,149,575, the disclosures of which are incorporated herein by reference.

A substernal placement may be used instead, with one finger 18/20 or the entire distal end of the lead (that is, the end distant from the canister 16) going beneath the sternum. Some examples of such placement are described in US PG Patent Pub. No. 2017/0021159, titled SUBSTERNAL PLACEMENT OF A PACING OR DEFIBRILLATING ELECTRODE, the disclosure of which is incorporated herein by reference. Still another alternative placement is shown in U.S. Provisional Patent Application No. 62/371,343, titled IMPLANTATION OF AN ACTIVE MEDICAL DEVICE USING THE INTERNAL THORACIC VASCULATURE, the disclosure of which is incorporated herein by reference.

The devices 14 and 16 may communicate with one another and/or with an external programmer 30 using conducted communication, in some examples. Conducted communication is communication via electrical signals which propagate via patient tissue and are generated by more or less ordinary electrodes. By using the existing electrodes of the implantable devices, conducted communication does not rely on an antenna and an oscillator/resonant circuit having a tuned center frequency or frequencies common to both transmitter and receiver. RF or inductive communication may be used instead. Alternatively the devices 14 and 16 may communicate via inductive, optical, sonic, or RF communication, or any other suitable medium.

The programmer 30 may optionally use a wand (not shown) and/or skin electrodes 32 and 34 to facilitate communication. For example, skin electrodes 32 and 34 may be used for conducted communication with an implantable device. For other communication approaches such as RF or inductive communication, the programmer 30 may use a programming wand or may have an antenna integral with the programmer 30 housing for communication. Though not shown in detail, the programmer 30 may include any suitable user interface, including a screen, buttons, keyboard, touchscreen, speakers, and various other features widely known in the art.

Subcutaneous implantable defibrillators may include, for example, the Emblem S-ICD System™ offered by Boston Scientific Corporation. Combinations of subcutaneous defibrillators and LCP devices are discussed, for example, in US PG Patent Publication Nos. 20160059025, 20160059024, 20160059022, 20160059007, 20160038742, 20150297902, 20150196769, 20150196758, 20150196757, and 20150196756, the disclosures of which are incorporated herein by reference. The subcutaneous defibrillator and LCP may, for example, exchange data related to cardiac function or device status, and may operate together as a system to ensure appropriate determination of cardiac condition (such as whether or not a ventricular tachyarrhythmia is occurring), as well as to coordinate therapy such as by having the LCP deliver antitachycardia pacing in an attempt to convert certain arrhythmias before the subcutaneous defibrillator delivers a defibrillation shock.

In some examples, rather than a therapy device such as the SICD 16 shown in FIG. 1, a second implantable medical device may take the form of an implantable monitoring device such as a subcutaneous cardiac monitor (SCM). An SCM may be, for example, a loop monitor that captures data under select conditions using two or more sensing electrodes on a housing thereof and/or attached thereto with a lead. Such monitors have found use to assist in diagnosing cardiac conditions that may be infrequent or intermittent, or which have non-specific symptoms. In the context of the present invention, an SCM, or even a wearable cardiac monitor, may be used in place of the SICD as described in any of the following examples.

Several examples focus on using a left ventricular LCP 14. However, some examples may instead use a right ventricular LCP 40, and other examples may include both the left ventricular LCP 14 and right ventricular LCP 40. In other examples, a three implant system may include two LCP devices 14, 40, as well as a subcutaneous device such as the SICD 16. In still other examples, an atrial-placed LCP (not shown) may also be included or may take the place of one of the ventricular LCP devices 14, 40.

Figure 2:
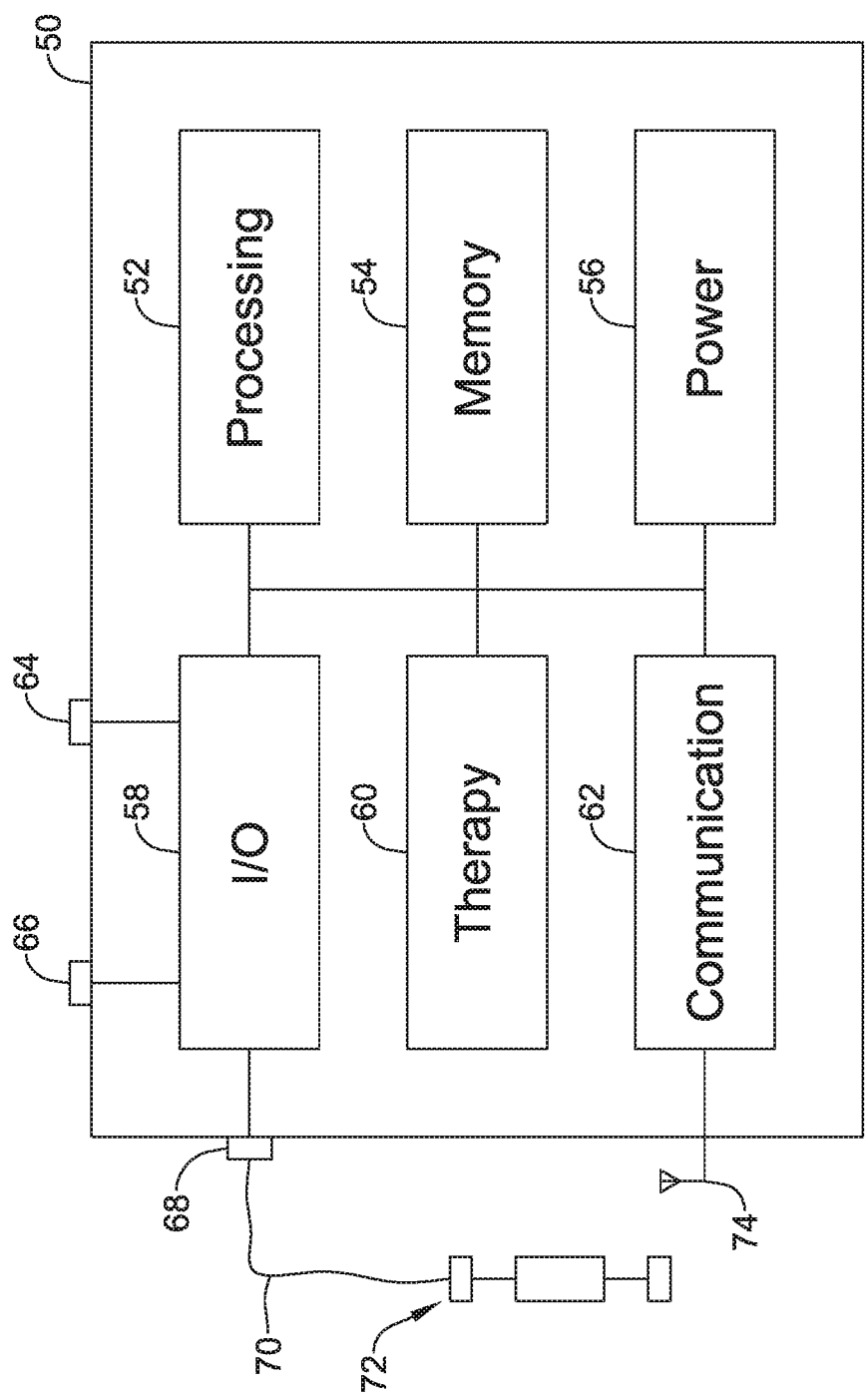
FIG. 2 illustrates a block diagram of an implantable medical device.

FIG. 2 illustrates a block diagram of an implantable medical device. The illustration indicates various functional blocks within a device 50, including a processing block 52, memory 54, power supply 56, input/output circuitry 58, therapy circuitry 60, and communication circuitry 62. These functional blocks make up the operational circuitry of the device. The I/O circuitry 58 can be coupled to one or more electrodes 64, 66 on the device 50 housing, and may also couple to a header 68 for attachment to one or more leads 70 having additional electrodes 72.

The processing block 52 will generally control operations in the device 50 and may include a microprocessor or microcontroller and/or other circuitry and logic suitable to its purpose. A state machine may be included. Processing block 52 may include dedicated circuits or logic for device functions such as converting analog signals to digital data, processing digital signals, detecting events in a biological signal, etc. The memory block may include RAM, ROM, flash and/or other memory circuits for storing device parameters, programming code, and data related to the use, status, and history of the device 50. The power supply 56 typically includes one to several batteries, which may or may not be rechargeable depending on the device 50. For rechargeable systems there would additionally be charging circuitry for the battery (not shown).

The I/O circuitry 58 may include various switches or multiplexors for selecting inputs and outputs for use. I/O circuitry 58 may also include filtering circuitry and amplifiers for pre-processing input signals. In some applications the I/O circuitry will include an H-Bridge to facilitate high power outputs, though other circuit designs may also be used. Therapy block 60 may include capacitors and charging circuits, modulators, and frequency generators for providing electrical outputs. A monitoring device may omit the therapy block 60 and may have a simplified I/O circuitry used simply to capture electrical or other signals such as chemical or motion signals.

The communication circuitry 62 may be coupled to an antenna 74 for radio communication (such as Medradio, ISM, or other RF), or alternatively to a coil for inductive communication, and/or may couple via the I/O circuitry 58 to a combination of electrodes 64, 66, 72, for conducted communication. Communications circuitry 62 may include a frequency generator/oscillator and mixer for creating output signals to transmit via the antenna 74. Some devices 50 may include a separate or even off-the shelf ASIC for the communications circuitry 62, for example. For devices using an inductive communication output, an inductive coil may be included. Devices may use optical or acoustic communication, and suitable circuits, transducers, generators and receivers may be included for these modes of communication as well or instead of those discussed above.

As those skilled in the art will understand, additional circuits may be provided beyond those shown in FIG. 2. For example, some devices 50 may include a Reed switch, Hall Effect device, or other magnetically reactive element to facilitate magnet wakeup, reset, or therapy inhibition of the device by a user, or to enable an MRI protection mode. A device lacking a lead may have plural electrodes on the housing thereof, as indicated at 64, 66, but may omit the header 68 for coupling to lead 70. In one example, a leadless device may use a header to couple to an electrode support feature that is attached to or wraps around the device housing.

Figure 3:
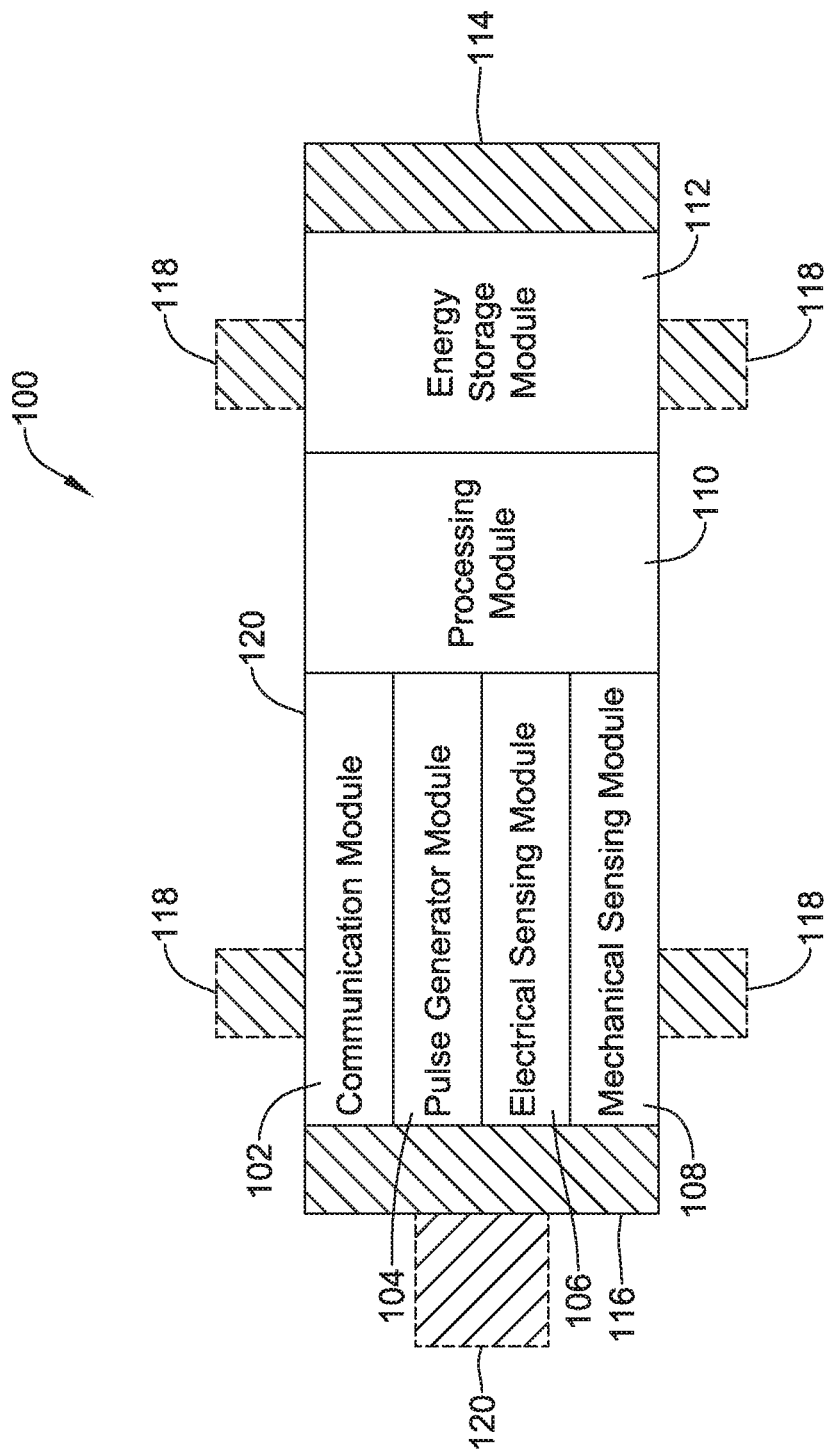
FIG. 3 shows an illustrative implantable leadless cardiac pacemaker.

FIG. 3 shows an illustrative LCP design. The LCP 100 is shown as including several functional blocks including a communications module 102, a pulse generator module 104, an electrical sensing module 106, and a mechanical sensing module 108. A processing module 110 may receive data from and generate commands for outputs by the other modules 102, 104, 106, 108. An energy storage module is highlighted at 112 and may take the form of a rechargeable or non-rechargeable battery, or a supercapacitor, or any other suitable element. Various details of the internal circuitry, which may include a microprocessor or a state-machine architecture, are further discussed in US PG Patent Publications 20150360036, titled SYSTEMS AND METHODS FOR RATE RESPONSIVE PACING WITH A LEADLESS CARDIAC PACEMAKER, 20150224320, titled MULTI-CHAMBER LEADLESS PACEMAKER SYSTEM WITH INTER-DEVICE COMMUNICATION, 20160089539, titled REFRACTORY AND BLANKING INTERVALS IN THE CONTEXT OF MULTI-SITE LEFT VENTRICULAR PACING, and 20160059025, titled, MEDICAL DEVICE WITH TRIGGERED BLANKING PERIOD, as well as other patent publications. Illustrative architectures may also resemble those found in the Micra™ (Medtronic) or Nanostim™ (St. Jude Medical) leadless pacemakers.

The device is shown with a first end electrode at 114 and a second end electrode at 116. A number of tines 118 may extend from the device in several directions. The tines 118 maybe used to secure the device in place within a heart chamber. Another attachment structure is shown at 120 and may take the form of a helical screw, if desired. In some examples, tines 118 are used as the only attachment features. Tissue attachment and retrieval features may be included in the LCP including those features shown in US PG Patent Publications 20150051610, titled LEADLESS CARDIAC PACEMAKER AND RETRIEVAL DEVICE, and 20150025612, titled SYSTEM AND METHODS FOR CHRONIC FIXATION OF MEDICAL DEVICES, the disclosures of which are incorporated herein by reference. Fixation and retrieval structures may instead resemble that of the Micra™ (Medtronic) or Nanostim™ (St. Jude Medical) leadless pacemakers.

Figure 4:
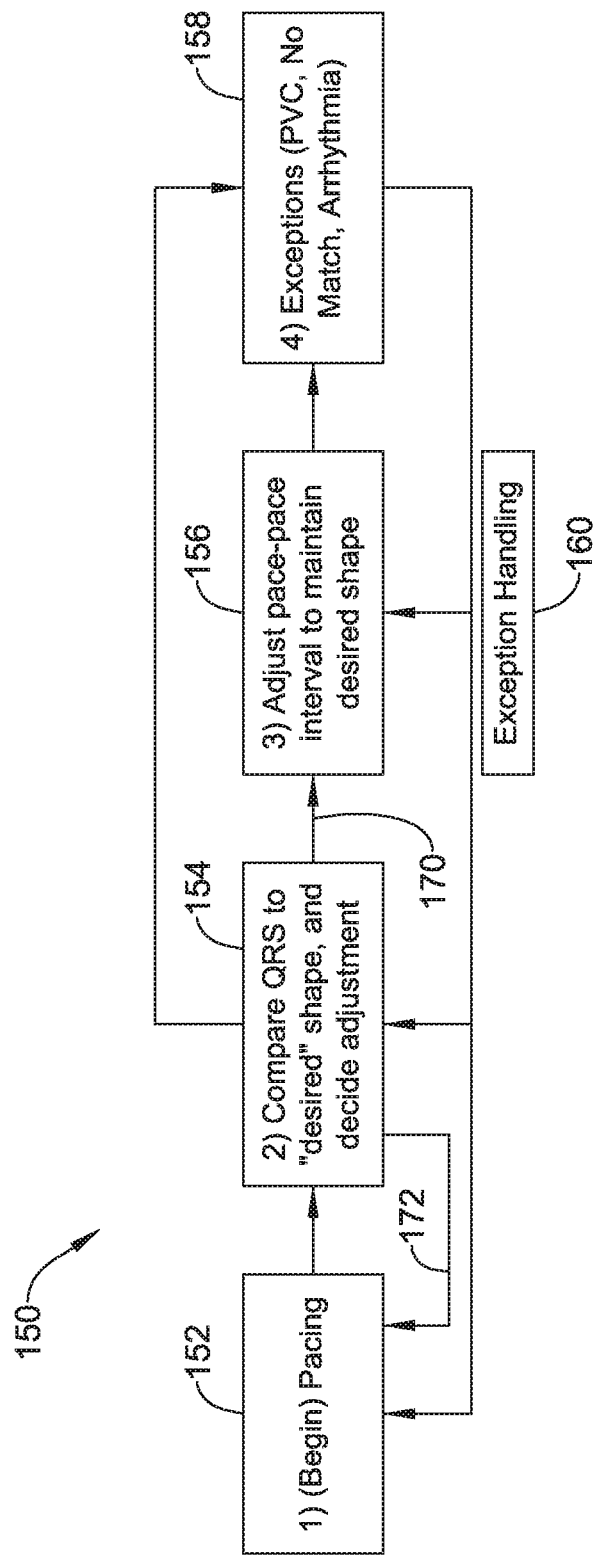
FIG. 4 shows an illustrative method of operation for a system.

FIG. 4 shows an illustrative method of operation for a system. The overall method 150 comprises steps that may be performed by each of first and second implantable medical devices operating in concert with one another. At block 152, a first medical device delivers one or more pacing pulses. Block 152 may be the beginning point with an initial pacing pulse delivery, or may appear in the middle of a looping methods as shown. The pacing pulses may be delivered for CRT purposes. In an example, the first medical device that performs pacing delivery at block 152 is an LCP. Pacing pulses may be monophasic or biphasic and delivered with any suitable pulse width and amplitude. The LCP performing pacing at block 152 may be placed in the left ventricle, though other placements (in the cardiac vasculature or right ventricle, for example) may instead be used.

In some examples, if block 152 is to deliver the first pacing pulse of a CRT therapy (that is, the first pacing pulse after some period of at least one cardiac cycle during which no pacing is delivered), specific rules may be applied. For example, the intrinsic cardiac rate may be determined by, for example, measuring the interval between R-waves for two or more recent non-paced cardiac cycles. The "first" pace can then be delivered at a reduced interval, such as in the range of 75% to 90% of the measured interval, or at a fixed reduction, such as in the range of 50 to 150 milliseconds less than the R-R interval. If desired, an in-clinic measurement may be made to determine, at rest, in one or more postures, or at rest and while exercising, the typical P-R interval for the patient, and the first pace therapy may then be delivered at a time determined by subtracting a portion (20% to 50%, for example) of that patient's typical P-R interval from the measured R-R interval. In still another alternative, to the extent an extracardaic device such as an SICD or SCM may detect the P-wave and calculate a typical P-R interval, the "first pace" may be delivered at a time that is approximately centered between the expected P-wave and the expected R-wave.

In an example, an in-clinic measurement may be performed to identify the P-R interval for the patient at a given R-R interval. An in-clinic P-R:R-R ratio is calculated and stored. Later, in the ambulatory context, a measured R-R interval is multiplied by the in-clinic R-R:R-R ratio, to yield a value for the expected P-R interval. This P-R interval is then reduced by a value in the range of 20% to 50% (40% for example) to give a foreshortening value. The "first pace interval" is calculated by subtracting the foreshortening value from the measured R-R interval. A first pace is delivered after expiration of the first pace interval following an R-wave. A second pace may be delivered following the first pace after an interval that is equal to the measured intrinsic R-R interval. Subsequent pace therapies are delivered at intervals that may be modified in light of the fusion promotion methods further described below.

At block 154, a second medical device, such as an SICD or SCM, senses for and obtains a QRS complex from the cardiac signal, and compares the QRS complex shape to a "desired" shape. The method in block 154 may occur as part of ordinary operation of the second medical device, which for either an SICD or SCM would typically include monitoring the cardiac signal to identify arrhythmias. The specific analysis at 154 may be triggered to include the comparison to the desired shape over and above analysis for arrhythmia detection. For example, analysis may be triggered by having the LCP that delivers the pace at 152 issue a communication to the second medical device indicating that a pace therapy has been delivered. Analysis may also be triggered by the second medical device being aware that that a pacing regimen for CRT is ongoing, rather than triggering on individual pace therapies. Analysis may also be triggered if the second device detects the pacing therapy delivery itself, which may be identifiable from within the cardiac electrical signal (a pacing spike may be observed), or may be identifiable using dedicated analysis such as a sensing channel having filtering or triggering analyses applied thereto intended to identify a pace therapy. For example, a pacing output may be a square wave output in the voltage or current domain and so may have specific frequency content different from that of the surrounding cardiac tissue, and a pace identification circuit be configured to identify the frequency signature of the pace output.

As discussed in further examples below, various analyses may be performed to determine a match, or mismatch, to the desired shape. For example, a template may be compared using difference of area, correlation waveform analysis (CWA), principal components analysis (PCA), wavelet transformation, etc. In other examples, specific features, such as slopes, width between identified points, the quantity and timing of inflection or turning points, amplitude, polarity type, or other features, may be analyzed. Using the result of the comparison, the second implantable device determines whether an adjustment is needed, as indicated.

For example, if the comparison determines that the detected QRS resembles a pace captured beat, rather than the desired fusion beat, an adjustment to the pacing parameters extend a pace to pace interval to allow the intrinsic signal to catch up and fuse with the pace. If the comparison determines that the detection QRS resembles an intrinsic beat, then the pace to pace interval may be shortened to help the paced beat catch up to the intrinsic signal and fuse with the intrinsic signal.

If an adjustment is needed, the method proceed to block 156 where the first medical device makes an adjustment to the pace to pace interval in order to maintain or re-impose the desired shape. For example, if the detected QRS is not a fusion beat, then the first medical device can adjust the pace to pace interval to preferably promote fusion by shortening (in the event of an intrinsic beat) or extending (in the event of a capture beat) the pace to pace interval.

If an exception occurs, the method jumps from either block 154 or 156 to exception handling 158. Exception handling 158 may handle cases in which a ventricular extra-systole (VES) takes place such as a premature ventricular contraction (PVC) or a premature atrial contraction (PAC), as shown below by FIGS. 15-16. Exception handling may accommodate a case in which no match to any of a fusion, non-paced, or purely paced beat can be found at 154 by, for example, restarting the pacing regimen, terminating pacing to determine if some other arrhythmia is taking place, and/or setting and/or annunciating an error code. In addition, an exception may occur if an arrhythmia is initiated, which may manifest as beats repeatedly occurring faster than the pacing can be delivered suggesting a tachyarrhythmia such as a conducted atrial tachycardia, atrial fibrillation, or ventricular tachycardia or fibrillation.

Exception handling may follow multiple paths as indicated at 160 by returning to any of blocks 152, 154, or 156. In some examples, if the QRS shape matches the desired fusion shape, rather than following patch 170 to go to block 156, the system may simply return to block 152 and await a next pace delivery, without adjusting pace to pace intervals at 156. In still another example, even if the desired shape occurs at block 154, the system may adjust pace to pace parameters to maintain dithering around an ideal pacing interval.

In an alternative example, rather than the second device determining whether and how to make an adjustment, the second device may communicate to the first device whether a match appears at block 154, and the first device may determine whether and how to make an adjustment using the match information. Various further examples follow.

Figure 5:
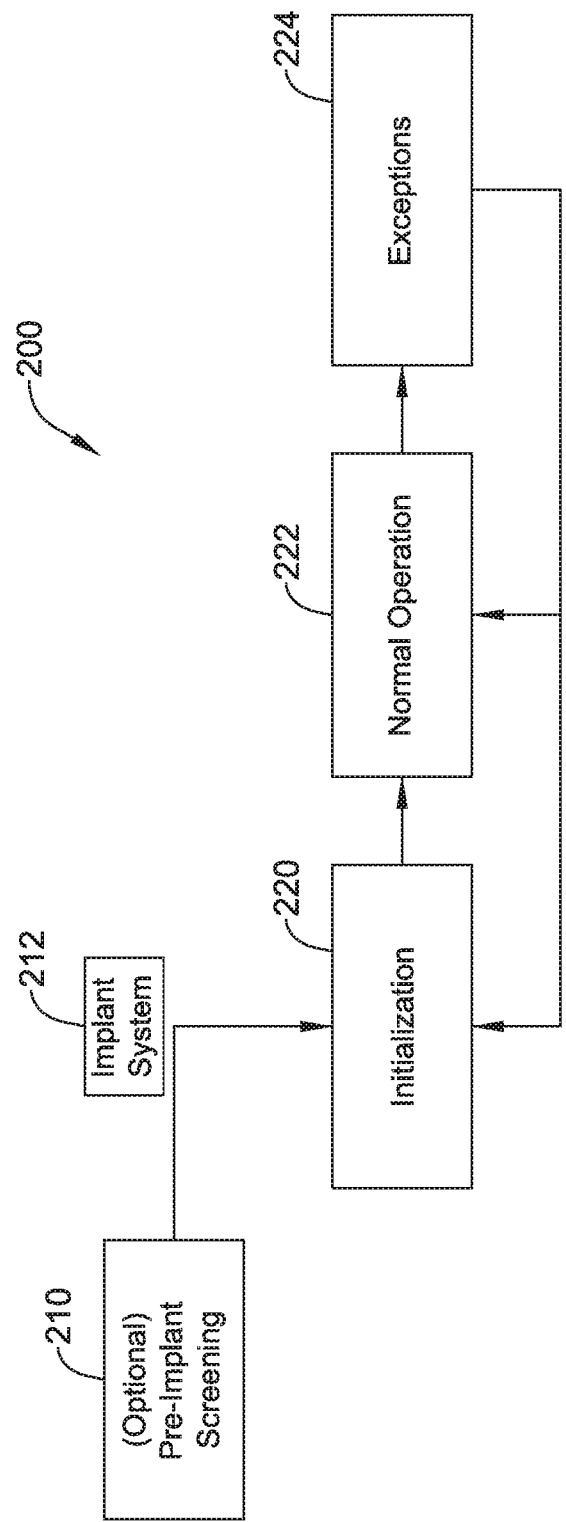
FIG. 5 shows an overall method of use of a system.

FIG. 5 shows an overall method of use of a system. The method 200 in this case goes back, optionally, to pre-implant screening, as indicated at 210. For example, the implantation of an SICD may occur following pre-implant screening for cardiac signal amplitude and/or signal to noise ratio, and/or to determine whether the patient's routine cardiac rhythm will be well managed using an SICD. Some example screening tools, metrics and methods discussed in U.S. Pat. No. 8,079,959, titled PATIENT SCREENING TOOLS FOR IMPLANTABLE CARDIAC STIMULUS SYSTEMS, and/or U.S. patent application Ser. No. 15/001,976, titled AUTOMATED SCREENING METHODS AND APPARATUSES FOR IMPLANTABLE MEDICAL DEVICES, the disclosures of which are incorporated herein by reference.

As noted in U.S. Provisional Patent Application Ser. No. 62/355,121 pre-implant screening may also determine whether the patient is well suited to have a combined LCP/SICD or LCP/SCM system for CRT by assessing the presence or absence of a P-wave. P-wave related screening may be optional with the present invention, as various examples rely on SICD or SCM analysis of the QRS complex (or other cardiac signal) to confirm fusion, rather than the appearance or timing of the P-wave.

The system(s) are then implanted at 212. Implantation may include the placement of an LCP on or in the heart, as well as placement of an SCM or SICD elsewhere in the patient such as between the ribs and the skin. The system may undergo intraoperative testing as is known in the art for each of LCP, SCM and SICD devices, to ensure adequate sensing configurations and/or therapy capability.

Next, the system undergoes initialization, at 220. Initialization may include, for example, the setting of various sensing and other parameters. Examples of initialization may include selecting of a sensing vector or combination of sensing vectors, such as in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH, and U.S. Pat. No. 8,483,843 SENSING VECTOR SELECTION IN A CARDIAC STIMULUS DEVICE WITH POSTURAL ASSESSMENT, the disclosures of which are incorporated herein by reference. Related concepts are also disclosed in US PG Patent Pub. Nos. 2017/0112399, 2017/0113040, 2017/0113050, and 2017/0113053, the disclosures of which are incorporated herein by reference. Methods as discussed in US PG Patent Pub. No. 2017/0156617, titled AUTOMATIC DETERMINATION AND SELECTION OF FILTERING IN A CARDIAC RHYTHM MANAGEMENT DEVICE, the disclosure of which is incorporated herein by reference, may be used as well for setting filtering characteristics.

Thus, initialization may include methods for selecting a sensing vector as shown by FIG. 6, below. In addition, initialization 220 may further comprise the identification of features characteristic of one or more of fusion beats, pace captured beats, and intrinsic beats, as illustrated below in FIG. 7. Initialization for an LCP may also include the setting of parameters for therapy including, for example, selecting pace shape, pulse width and/or amplitude. If plural LCPs are included in a system, the relative timing between pace deliveries and other suitable features may be set as well.

Once initialization 220 is completed, normal operation can occur as indicated at 222. Normal operation may include operation as in FIGS. 10-14, below. Such operation may include CRT delivery in which a first device delivers pacing pulses at predetermined intervals relative to previous pacing pulses; a second device monitors cardiac electrical signals to determine whether pacing therapy is causing: one or more fusion beats; one or more pace captured beats; or one or more intrinsic beats; and the second device selectively communicating to the first device to adjust the predetermined interval. In other examples, the second device may simply determine whether fusion is taking place, and if so, preserving an existing configuration, or if not, adjusting an existing configuration.

As needed, additional exceptions may be handled at 224. Exceptions may occur if sensed cardiac signals do not match any of a fusion, captured, or intrinsic beat template, for example. Exceptions may also occur if an arrhythmia such as a ventricular or atrial tachyarrhythmia or fibrillation occurs. The exceptions 224 may allow return to normal operation 222 once handled, or may require re-initialization 220.

FIG. 6 illustrates selected factors for sensing configuration. As illustrated at 250, sensing vector configuration is to be performed during this part of the initialization of a system. The amplitudes of relevant cardiac signals and signal features may be used, as indicated at 252. Signal to noise ratio 254 may also be considered. The consistency 256, or lack thereof, of the cardiac signals captured using a particular sensing configuration (vector, filtering, gain, etc.) may be observed and used as well. For example, if the cardiac signal appears to vary significantly in a given sensing vector from one cardiac complex to the next, that particular sensing vector may be rejected due to lack of consistency.

Selected factors 252, 254, 256 may be used to analyze a plurality of sensed signals along one or a number of cardiac sensing vectors. For example, as shown in FIG. 1, the SICD or SCM 16 may include an electrically active canister and a lead 18/20 having a number of electrodes 22, 24, 26, 28, and others shown but not numbered. Each pair of electrodes may define a sensing vector, with the different sensing vectors available having different characteristics given their position relative to the heart and each other.

As shown on the right-hand side of FIG. 6, the plural sensing vectors may provide different looking cardiac signals, as shown at 260, 262, 264, 266. Some have greater peak amplitudes, and some have signals with relative peaks that may represent noisier signals. The amplitudes 252 may include, for example, the amplitudes shown at 270 (R-wave peak), 272 (T-wave peak), and/or 274 (P-wave peak). Signal to noise ratio may be assessed by comparing the peak at 270 to those at 272 and/or 274, with lower ratios potentially making it harder to distinguish and accurately detect R-waves rather than the P-waves or T-waves. Consistency for a given vector may be observed by, for example, comparing QRS complex at 280 to a subsequent QRS complex 282. More consistent QRS complex shape may be helpful. In the example shown, as noted by the circle, the signal at 260 appears to provide a better sensing signal than the other signals 262, 264, 266, based on the QRS at 280 matching the QRS at 282, while also having large amplitude 270 both in absolute terms as well as when compared to the T-wave 272 and/or P-wave 274. These and/or other factors may be used to determine a sensing configuration.

Figure 7:
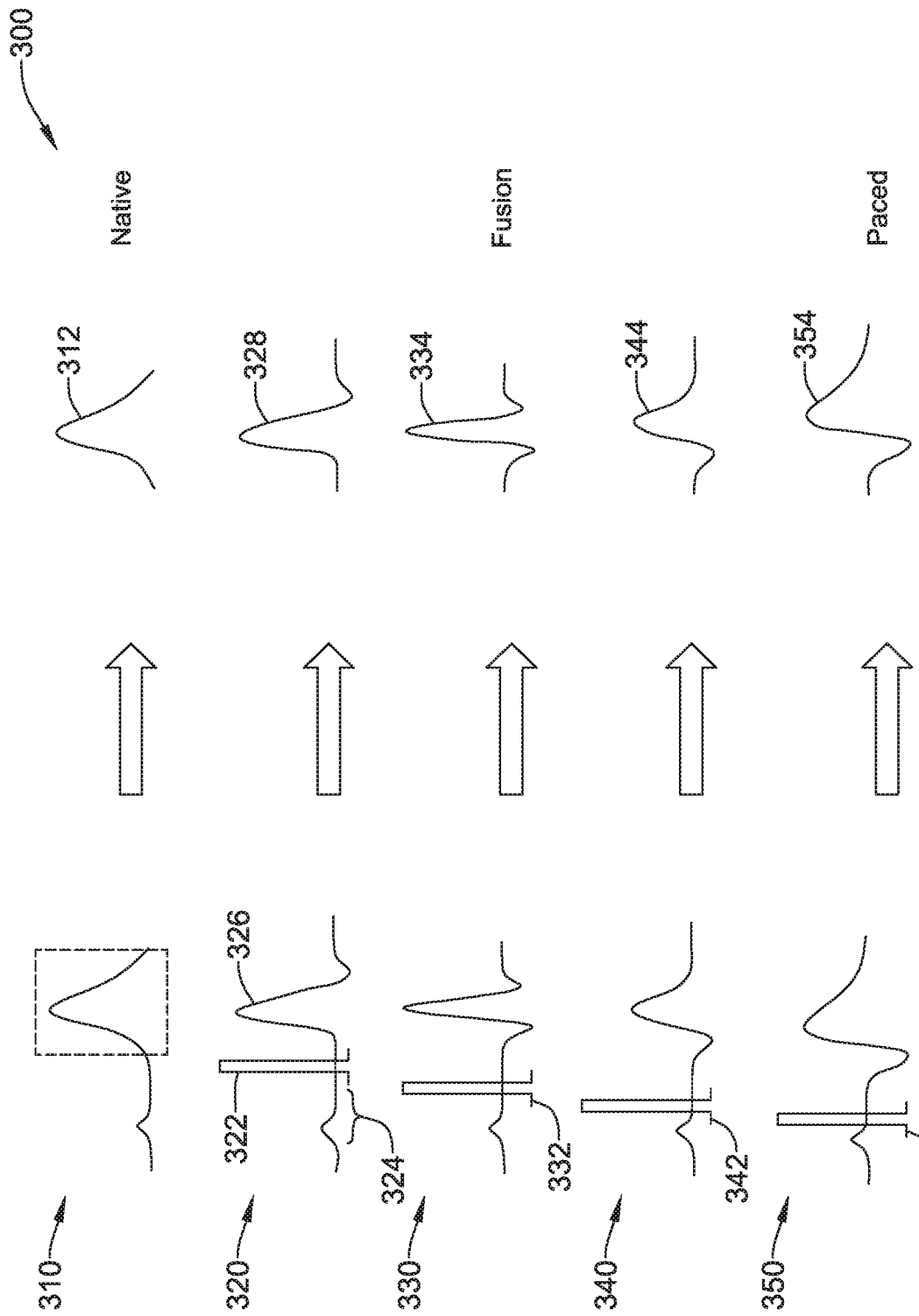
FIG. 7 shows in graphical form the generation of plural templates for assessing fusion.

FIG. 7 shows in graphical form the generation of plural templates for assessing fusion. In an illustration, as shown on the left side of the figure, a number of different pacing parameters are attempted, using different timing relative to one or more features. In an illustrative example, the various timings shown for the delivery of pacing pulses are accomplished by first determining the intrinsic interval between R-waves (R-R interval), and then delivering pace pulses after R-waves or QRS complexes at intervals that are shorter than the intrinsic rhythm. For example, the pacing outputs may be delivered at various intervals such as 100, 150, 200 and 250 milliseconds shorter than the intrinsic R-R interval. Other intervals and quantities of intervals may be used. For example, the pacing output may be generated at across a range from 100 to 250 milliseconds less than the intrinsic R-R interval with a stepped process where the intervals are modified by 5 to 50 millisecond for each step. For example, after several intrinsic beats, a single pace at a lesser interval may be delivered, after which the intrinsic rhythm may resume. In another example, several paced beats at the lesser interval may take place. In another example, the pacing attempts at different timing may be performed under physician observation or supervision. In yet another example, if the P-wave can be sensed for at least initialization purposes, different timing relative to the P-wave may be attempted.

Data is captured by the SICD or SCM during this pacing regimen of the LCP. That data can be used to generate several templates in the manner illustrated by FIG. 7. For example, an intrinsic, non-paced signal is shown at 310; a window may be defined for capturing an R-wave template, and a native R-wave template is then obtained as indicated at 312.

An additional template is formed as shown at 320, in which some fusion occurs but the pace 322 is later 324 than appropriate to generate fusion, yielding an R-wave at 326 that is used for template 328. It may be noted that for purposes of illustration, simple monophasic pace pulses are shown in the figures. In implementation, monophasic, biphasic, or other multiphasic pace pulses may be delivered in any desired polarity and may take forms including constant, ramped, or decaying current or voltage controlled therapies.

Another template is formed at 330, this time with fusion based on well-timed pace 332. At 340, the pace 342 occurs too early for fusion, yielding another template at 344 that does not show fusion. Finally, at 350, the pace 350 occurs early enough that no fusion occurs, instead resulting in a pure capture of the left ventricle (LV), assuming for this example that the LCP is in the LV.

A total of five templates are suggested in FIG. 7; fewer or more may be used in some examples. In one example, the native 312, fusion 334, and paced 354 templates are all that is formed. In another example, the in-between templates 328, 344 are formed along with the fusion template 334. In yet another example, only the fusion template 334 and one of the other templates 312, 328, 344, 354 are formed.

To accomplish template formation, it may be desirable to have the LCP and the SICD or SCM communicate with one another to indicate which pace timing is being attempted during the process. For example, the LCP may determine an intrinsic R-R interval, and may then communicate to the SICD or SCM that it is about to deliver a pace pulse at an interval that is 100 milliseconds less than the intrinsic interval, which could be done to generate template 328. It should be understood that relying on the intrinsic R-R interval to achieve desired fusion is not a long term approach to fusion promotion, insofar as once pacing begins to take place, the intrinsic R-R interval would no longer be available.

It may also be desirable to perform the template formation in a setting that is relatively controlled. For example, one or more of the LCP and SICD/SCM may be configured to determine that the patient is at rest prior to gathering the templates by using the outputs of an activity or motion sensor (such an accelerometer), and/or confirming that the patient's cardiac rate indicates a resting state. Respiration and/or posture may also be monitored. If desired, separate templates may be captured for different postures in a clinical setting with physician supervision, using methods as in U.S. Pat. No. 8,200,341, titled SENSING VECTOR SELECTION IN A CARDIAC STIMULUS DEVICE WITH POSTURAL ASSESSMENT, the disclosure of which is incorporated herein by reference. On the other hand, the implantable devices (LCP and/or SICD/SCM) may be configured to determine a patient posture, and may perform template formation methods for each of several sensed/determined patient postures over time.

The example at 300 may use signals from multiple sense vectors in combination with one another. In another example, the method 300 may determine a first template for a first waveform type using a first sensing configuration, and a second template for a second waveform type using a second sensing configuration. For example, the native template 312 may be generated on a sensing vector that does not pick up the pacing artifact since a pacing artifact is likely to occur close to the cardiac complex itself and could make a match relatively easy to obtain; the paced beat 354, on the other hand, occurs well after the pacing therapy stimulus and therefore a template captured using a sensing vector that can observe the pacing artifact may be useful.

The template formed may be a stored shape, that is, a time-ordered series of amplitude values. The template may instead be stored as a mathematical transform of the original signal using, for example, wavelet analysis, principal components analysis, or other transform. Alternatively, the template may take the form of a set of signal features as further illustrated below.

The resulting library of templates may be updated periodically if desired. For example, a new library of templates may be generated at each clinical follow-up visit, or on a daily, weekly, or monthly basis. In addition to periodic updating, the template library may be updated as needed. For example, if no templates can be matched using the below methods for some period of time, the library may be regenerated.

Figure 8:
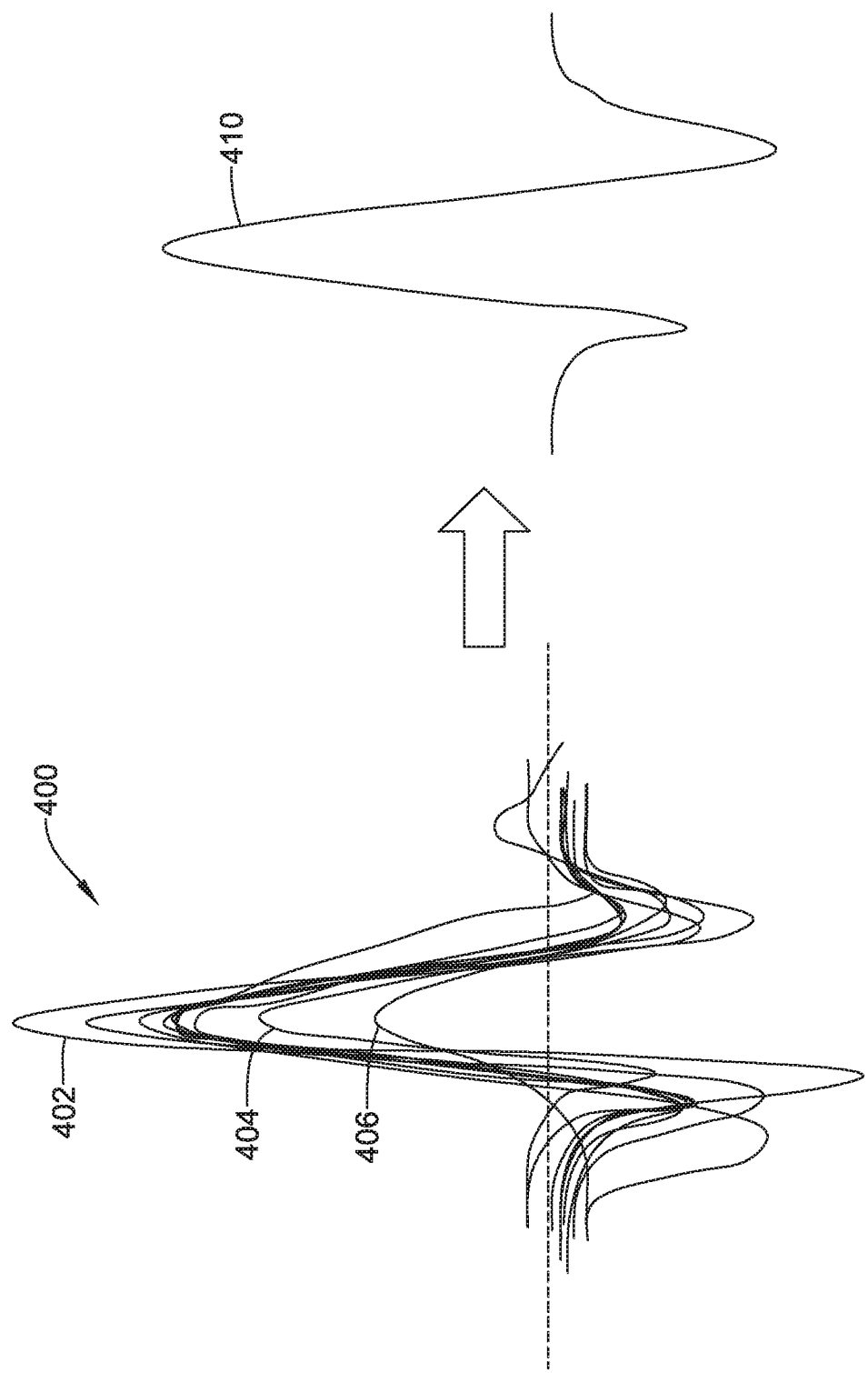
FIG. 8 illustrates the generation and use of a composite cardiac signal.

FIG. 8 illustrates the generation and use of a composite cardiac signal. A composite cardiac signal may be used to assist in initialization processes, or other methods, of an implanted system. Electrical signals are sensed for a plurality of cardiac cycles and then aligned with one another using a fiducial point such as the R-wave peak. The result is as shown at 400, where several individual signals 402, 404, 406 overlie one another. Any suitable processing technique may then be used to create a composite signal as shown at 410 from the plural signals. For example, the composite 410 may be the mean or median of the other signals 402, 404, 406 at each point in time. The composite signal 410 may be used for vector selection and/or may be used to generate the templates of FIG. 7 by capturing a plurality of paced cardiac cycles in which similar pace timing is used.

Figure 9:
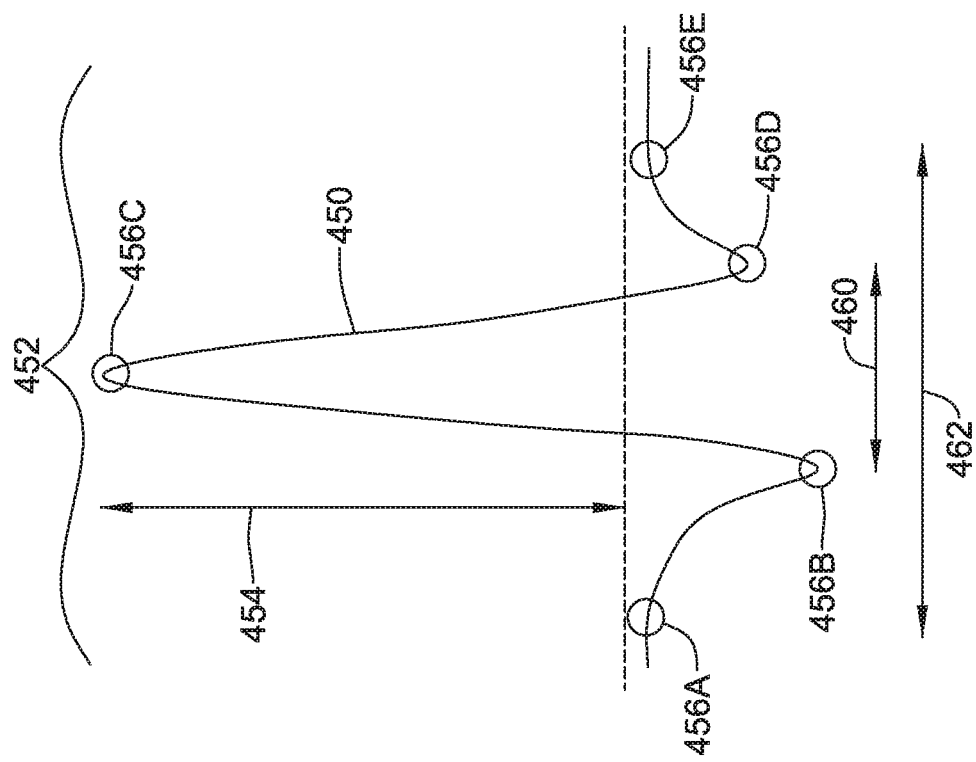
FIG. 9 illustrates features of a cardiac signal that may be used for assessing fusion.

FIG. 9 illustrates features of a cardiac signal that may be used for assessing fusion. One or several of these features may be stored as the "template" of cardiac fusion. For example, the signal captured at 450 may be stored as the time ordered series of samples, or a mathematical transform thereof (wavelet, principal components, etc.) spanning some portion of or all of window 452. Alternatively, one or more features may be stored such as the amplitude 454, a set of individual points 456(A), 456(B), 456(C), 456(D), 456(E), stored in relative or absolute terms based on timing and amplitude relative to a baseline or each other. The points to store may be, as shown, turning points (first derivative zeroes) or may be instead inflection points (second derivative zeros). Additional features may include one or more widths, such as those highlighted at 460, 462. In some examples, a combination of the width 460 and the overall signal window 452 may be used to assess fusion by indicating, for example, that a signal that matches the overall signal window 452 is deemed a fusion beat, as well as a signal that matches the width 460 and has polarity of a predetermined form. In one example, a template takes the form of the overall signal 452 within a selected window between points 456(B) and 456(D), stored as a time ordered series of amplitudes scaled relative to the amplitude 454 of the peak 456(C).

Referring back to FIG. 5, the illustrations of FIGS. 6-9 may all take place as part of the initialization process 220. Next the system moves to "normal operation", 222, with the illustration of FIG. 10.

Figure 10:
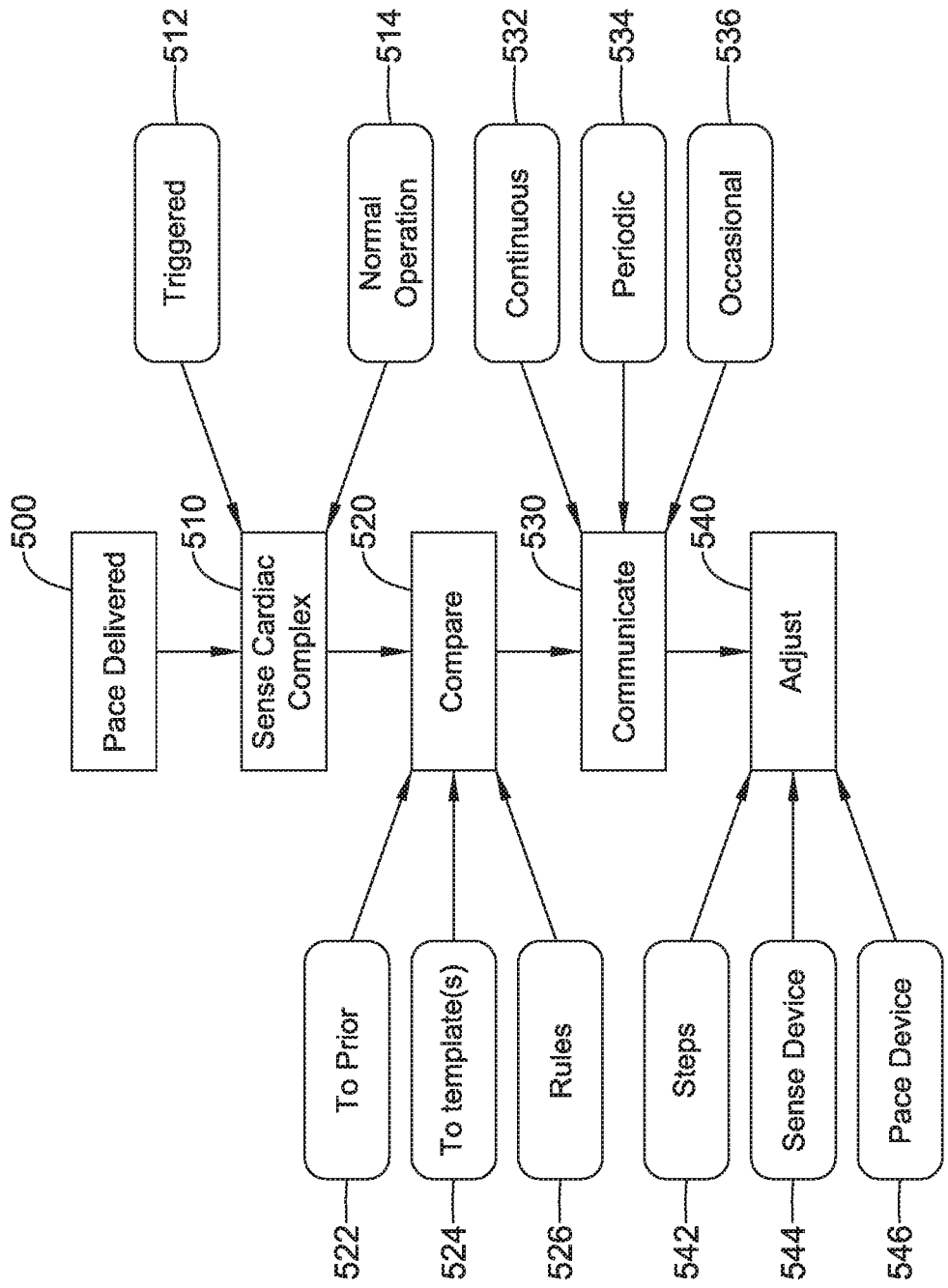
FIG. 10 is a block diagram illustrating a method of operation for a system.

FIG. 10 is a block diagram illustrating a method of operation for a system. A pace therapy is delivered at 500. In an example, the pace therapy 500 is delivered by an LCP disposed to contact and/or stimulate the left ventricle of a patient.

Next, a cardiac complex is sensed, as shown at 510. The cardiac complex may be sensed at 510 by an SICD or an SCM. The sensed cardiac complex 510 may be sensed by the SICD or SCM being triggered by delivery of the pace therapy at 500 as, for example, may take place if the SICD or SCM is configured to specifically detect a pacing output or, alternatively, if the SICD or SCM receives a communication from an LCP that the pace therapy delivery 500 is to occur at a specific time.

More likely, however, the SICD or SCM may sense the cardiac complex at 510 through normal operation 514. For example, the SICD or SCM may use an R-wave detection method in which a sensed signal is compared to a time varying threshold. Illustrative examples may be found in U.S. Pat. No. 8,565,878, titled ACCURATE CARDIAC EVENT DETECTION IN AN IMPLANTABLE CARDIAC STIMULUS DEVICE, the disclosure of which is incorporated herein by reference.

Next, the sensed cardiac complex from 510 is compared 520 to a template or set of feature characteristics indicative of fusion. For example, a sensed cardiac complex from 510 may be compared 520 to a prior sensed cardiac complex 522. The sensed cardiac complex from 510 may be compared 520 to one or more templates 524. In still another example, the sensed cardiac complex from 510 may be compared 520 to one or more rules 526 specifying, for example, width, amplitude or other characteristics of one or more peaks, inflection points or other features of the sensed cardiac complex. A set of specific examples follow, after the rest of FIG. 10 is explained, illustrating how each of 522, 524, 526 may be used.

Blocks 510 and 520 may be performed by an SICD or SCM device. Next, a communication 530 may issue from the SICD or SCM to the LCP. Such communication may be continuous 532—that is, after every pace delivery and/or sensed cardiac complex. Alternatively, communication may be periodic 534, occurring at set intervals. Preferably, however, communication is occasional 536, being issued when it is determined that some element of the operation of the LCP needs to change. The communication may indicate an adjustment as described below at 540, to the pacing interval and/or timing or may indicate that the pacing interval and/or timing is already providing desired fusion. In one example, the occasional or periodic communication 534, 536 is tied to how often the comparison 520 is performed, where the comparison may be performed using a composite cardiac signal (FIG. 8) that may be calculated only every so often such as after at least two cardiac cycles have occurred since a last calculation.

For example, the communication 530 may indicate that an intrinsic beat has been detected, and so pacing should be delivered earlier and/or with a different level of energy (greater or different combination of amplitude or pulsewidth). Alternatively, the communication 530 may indicate that fusion has not been detected, and that it appears the pacing should take place earlier to attain desired fusion. In another example, the communication 530 may indicate that desired fusion has been attained, and so settings should be preserved. As an alternative, the communication may indicate that desired fusion has been attained and a dithering protocol, in which pacing intervals are increased and/or decreased to continuously modify the pacing therapy while staying close to desired fusion, should be initiated. In another example, the communication may indicate that the sensed cardiac complex does not suggest desired fusion, and it appears the pacing should take place later to attain desired fusion. In yet another example the communication may indicate that LV capture has been detected, and so the pacing should take place later—at a longer interval—to attain desired fusion.

Next, the method includes the LCP adjusting pacing, if requested by the communication at 530. Not shown on FIG. 10 is the option to make no adjustment, but it should be understood that a no-adjustment step may also take place to conclude the method. Adjustments may come in several forms. A step 542 approach to adjustment may be made, in which a change in the pacing interval, or other characteristic, is made at a predefined step size, such as by moving the pace therapy timing by 5 to 50 milliseconds, or more or less, to either extend or shorten the pace-pace interval.

Alternatively, the sensing device (the SICD or SCM) may calculate a proposed adjustment to pace timing, as indicated at 544, using device history or information related to the pace timing used to generate the various templates shown in FIG. 7, above. For example, the sense device may determine that a template that reflects pace delivery 100 milliseconds too early is the best match to the sensed cardiac complex, and so a 100 millisecond adjustment to delay the pace therapy may be calculated and communicated.

In still another alternative, the pace device may calculate an adjustment to pace timing as indicated at 546, again using device history or information related to the pace timing used to generate the various templates shown in FIG. 7, above. In an example, the pace device 546 may receive data indicating a degree of match to various templates or other rules, and may then calculate its own adjustment.

The system would then wait for the next pace delivery to occur.

In an illustrative example, the compare step at 520 may take the sensed cardiac complex from 510 and compare to one or more of the templates identified above in FIG. 7. Depending on which template has the best match, a determination of fusion, intrinsic beat, or captured beat, is made using the comparison at 520. Next, using a continuous communication 532, the SCID or SCM communicates the results of the comparison to the LCP, and the LCP calculates an adjustment at 546 (if needed), or makes a step adjustment 542. Alternatively, using occasional communication 536, the SICD or SCM communicates the results if no match to the fusion template is found; otherwise, no communication takes place. In still another alternative, the SICD or SCM calculates and adjustment at 544 after several cardiac cycles take place, and periodically 534 communicates an adjustment (at, for example, 2 second to 200 second intervals, or shorter or longer) based on several template 524 or rule-based 526 analyses.

In another illustrative example, a comparison to prior detected cardiac complex 522 is used to maintain fusion once it is attained. For example, the templates 524 may be used in a first iteration or several iterations of the method in FIG. 10. Once fusion beats are identified, then comparison to the templates may be replaced with comparison to a prior cardiac complex 522. As long as the beats match consecutively, the device may conclude that fusion is preserved. For this example, the templates 524 may be used to confirm, from time to time, that the operation has not deviated from fusion. Communication could take place on both periodic and occasional bases—with periodic communication 534 to confirm appropriate pace timing, and occasional communication 536 if fusion has stopped occurring.

In yet another illustrative example, the rules 526 may be used. Referring to FIG. 9, a fusion beat rule may be defined for a given patient by determining the width 462 of fusion beats, combined with the relative amplitudes of turning points 456(B) and 456(D), scaled for amplitude 454, with an additional rule requiring negative polarity for each of 456(B) and 456(D) and positive polarity for point 456(C). The sensed cardiac complex from 510 is analyzed for the relevant widths, relative amplitudes, and specified polarities as a set of rules 526. If all rules are met, then fusion is determined to be present. If fusion is not present, referring back to FIG. 7, point 456(D) may disappear or move well away from the R-wave peak 456(C), meaning that width 462 would increase greatly. Therefore, for this example, width 462 may be used to indicate that an LV pace-captured beat morphology has been detected and the pace interval should be increased to attain better fusion. If 456(B) and/or 456(D) cease to have negative polarity, the polarity rules would be violated in this example. A device may conclude that the nature of the violation suggests a native beat morphology, and so the pace interval would be decreased to attain better fusion.

Figure 11:
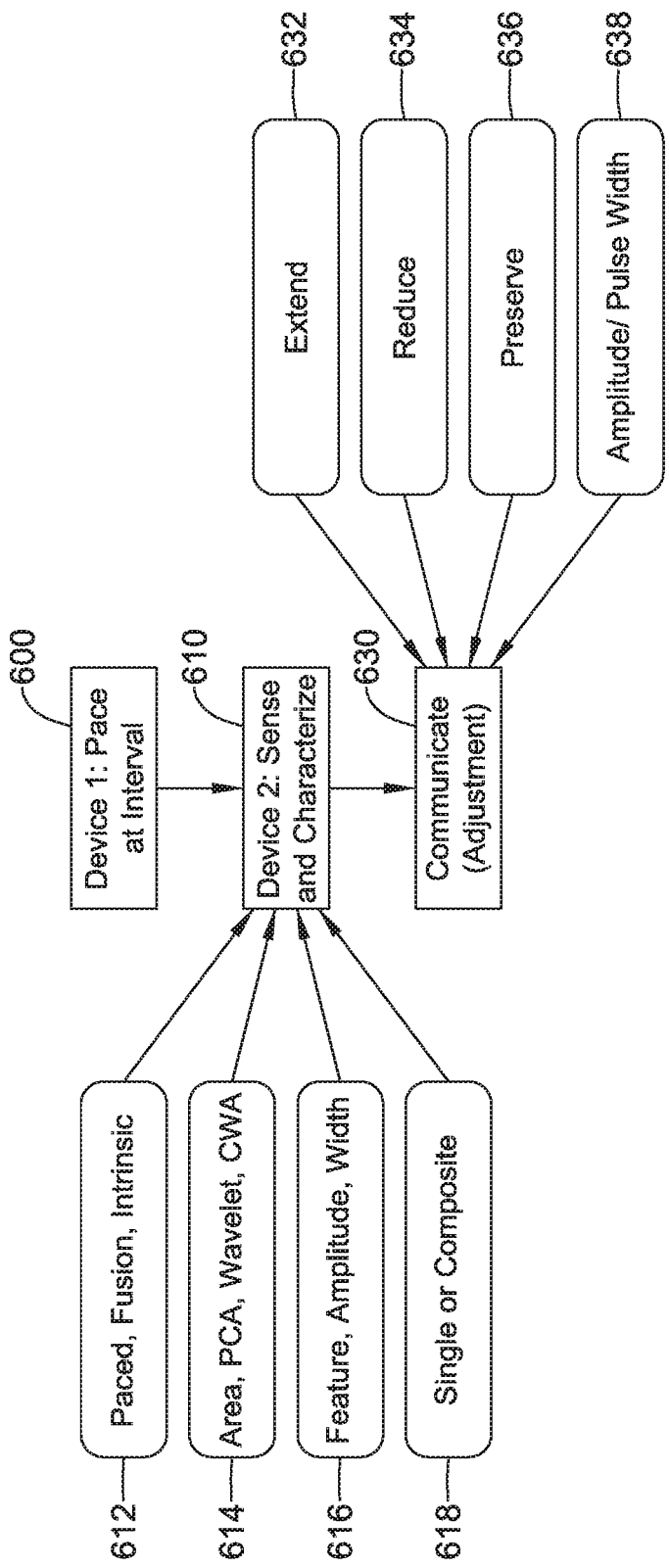
FIG. 11 is a block diagram illustrating a method of operation for a system.

FIG. 11 is a block diagram illustrating a method of operation for a system. This example shows a system level view. At 600, a first device delivers a pace therapy at an interval relative to a prior fiducial. The prior fiducial may be an R-wave peak or other feature of the cardiac electrical signal. The prior fiducial may instead be a prior pace therapy.

At 610, a second device senses and characterizes the cardiac response to the pace delivered in block 600. Various aspects of the sensing and characterization are noted to the left. Outcomes of the characterization are noted at 612 and may include, for this example, a determination of pace captured beat, fusion, or intrinsic morphology. Alternatively, block 612 may include simply characterization of fusion or no fusion. Other characterization sets are noted below and may be used instead of that shown at 612.

The manner of performing characterization may take several forms. If template data is stored and compared to the current cardiac cycle data, this may occur using one of several shape comparison methods noted at 614 including difference of area, principal components analysis (PCA), wavelet transforms, or correlation waveform analysis (CWA). The comparisons at 614 may also be tiered by, for example, reserving more computationally intensive comparisons (PCA, wavelet or CWA) for use in relation to non-fusion templates if/when a difference of area analysis comparing the current cardiac cycle to a fusion template fails to yield a match.

If, instead, a rule set is used to perform characterization, some details that may be used are noted at 616. These may include, for example signal features (such as finding turning points, inflection points, patterns of such points), amplitude (s), and/or width. Some illustrations are shown above in relation to FIG. 9. The characterization at 610 may make use of single cardiac cycle waveforms or composite waveforms as indicated at 618, with composite waveforms possibly taking a format as shown above in FIG. 8.

Finally a communication is made at 630. As noted with reference to FIG. 10, communication may be done on each cardiac cycle, or at periods or in response to selected conditions. In some examples, Device 2 calculates an adjustment and communicates a message stating what adjustment is to be made. For example, Device 2 may calculate and communicate that the pace-pace interval should be extended 632, reduced 634, or preserved 636. In other examples, Device 2 may indicate a different analytical result, such as by communicating a degree of match to one or more templates. Device 1 may then calculate its pacing adjustment by which it may extend 632, reduce 634, or preserve 636 a pace-pace interval.

In some examples, additional adjustments may be communicated to change amplitude and/or pulsewidth 638, particularly if there an intrinsic beat is detected suggesting a lack of capture. One such example would have Device 2 determining when the pace therapy was delivered relative to a detected R-wave or QRS complex; if the pace therapy was delivered at a time that should have caused capture or even a fusion event to take place, then Device 2 may conclude that a detected intrinsic beat occurred due to failure to deliver a pacing pulse of sufficient strength. Thus, Device 2 would indicate that amplitude and/or pulse width may be adjusted, as indicated at 638.

In an alternative illustration, block 612 may consider a current and prior characterization by having outcomes of fusion, no fusion (better)—which would indicate that the morphology of the current cardiac cycle is closer to a fusion morphology than a prior cycle, or no fusion (worse)—indicating that the morphology of the current cardiac cycle is more different from a fusion morphology than a prior cycle. In the event that fusion is identified, dithering change or no change may be communicated in block 630.

A "dithering" change is intended to convey dynamic adjustment to the pacing intervals, making them shorter and/or longer over time to attain "best" fusion. A dithering change may shorten or lengthen the pace-pace intervals until the morphology changes enough to reduce the match to the desired fusion beat. Further categorization of the characterization of the detected beat may be used in conjunction with dithering by including categories for "fusion (better)" and "fusion (worse)" to indicate that a fusion morphology was determined and was either more correlated (better) or less correlated (worse) than a preceding characterization. Dithering may be omitted in some examples.

If a non-fusion morphology is identified, the device history would next be considered. For example, if a preceding cardiac cycle has a non-fusion morphology, and an adjustment was made to extend or shorten the pace-pace interval before the current cardiac cycle, and the current cycle is characterized as no fusion (worse), then the prior change would in pace-pace interval would be reversed. On the other hand, if the current cycle is characterized as no fusion (better), then whatever change was made after the prior cardiac cycle would be repeated by further extending or shortening the pace-pace interval. With this example, a single template could be used, rather than multiple templates. In this example, both current cardiac cycle and historical data may be used to establish a trend and/or to determine, based on prior steps, what the next step to attain desired fusion would be.

Figure 12:
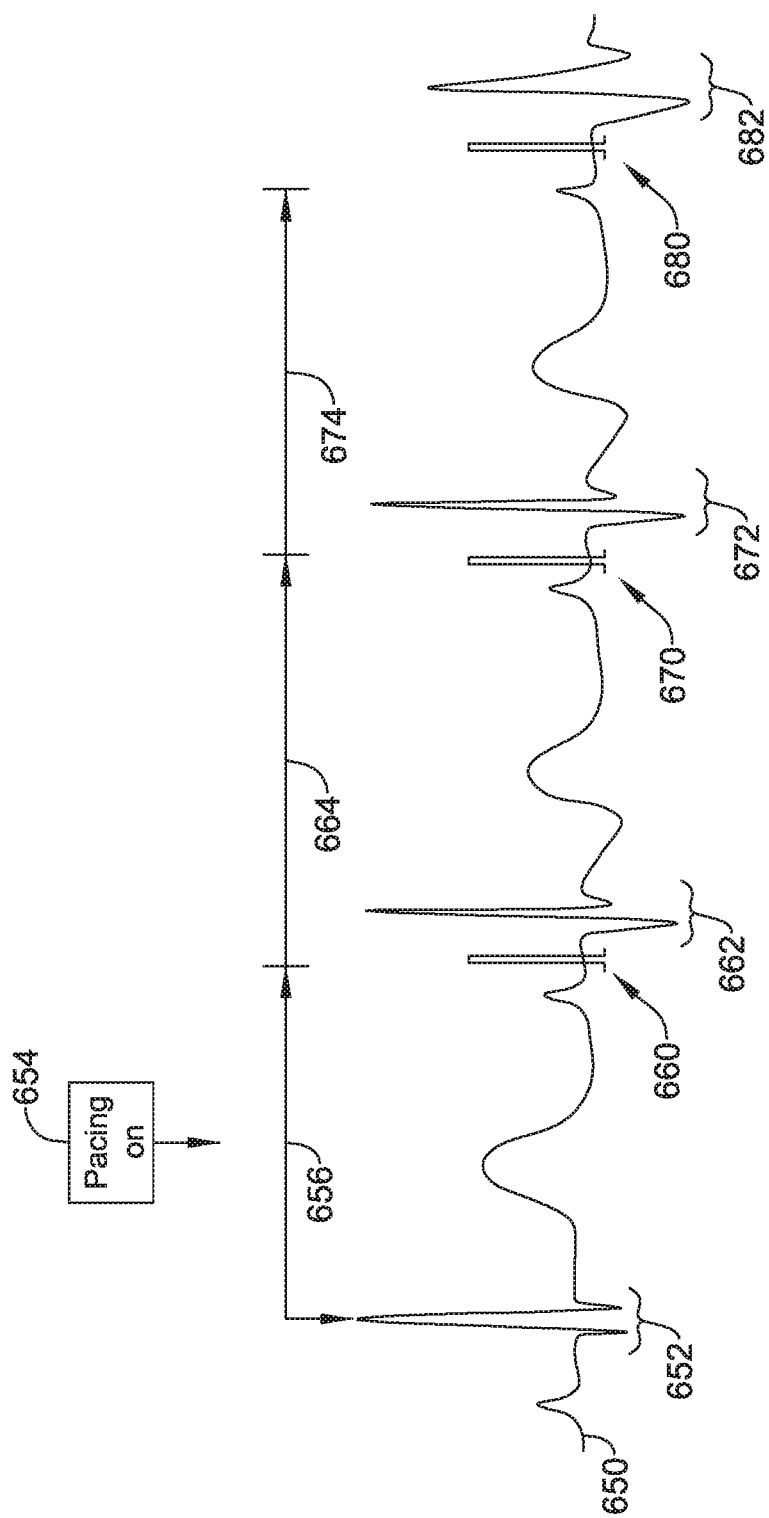
FIG. 12 illustrates pacing for fusion purposes.

FIG. 12 illustrates pacing for fusion purposes. The sensed cardiac signal is shown at 650, taking the form of a signal as may be sensed by an SICD or SCM. An intrinsic R-wave is shown as part of a QRS complex at 652. Pacing is indicated as "on" at 654; the timing of block 654 is merely illustrative and may occur at any time prior to the pace delivery at 660.

As shown at 660, a pace therapy is delivered. This "first" pace following the intrinsic QRS at 652 is delivered after expiration of an initial interval 656. The initial interval 656 may, as described above, be calculated by use of determining an expected P-R interval (or by measuring, if the P-wave can be detected), and discounting the P-R interval by some amount to yield a foreshortening factor. Interval 656 may equal to the intrinsic R-R interval calculated for one or more cardiac cycles prior to QRS complex 652, less the foreshortening factor.

If the first pace therapy 660 is delivered at an appropriate time, the following QRS complex will have a morphology typical of fusion as shown at 662. The shape will be different at 662 than at 652 if fusion is generated. For example, in this particular sensing vector view of the heart, the R-wave peak is narrower, and follows a more negative Q wave, than the intrinsic QRS complex at 652. If the first pace therapy 660 is too late, or if the therapy 660 is delivered at too low an energy, for example, the waveform may not change at all; on the other hand, if the first pace therapy 660 is too early, an LV pace capture waveform may appear instead. For purposes of the present invention, failure to generate fusion with the first pace delivery is acceptable; the aim is to enhance fusion pacing in a series of therapy deliveries over time. Once fusion is attained, the goal changes maintaining fusion.

Following pace therapy 660, a pace-pace interval 664 expires, leading to delivery of a next pacing pulse at 670. In the first iteration of pace-pace intervals at 664, the interval may be set equal to the intrinsic R-R interval measured for one or more cardiac cycles preceding QRS complex 652. If the pace-pace interval 664 is appropriate for fusion, the QRS complex at 672 will have similar morphology features as the prior fusion QRS complex 662, which is the case in the example shown. If the morphology at 672 did not match the fusion morphology and instead resembled an intrinsic beat morphology, as decided by the SICD or SCM, then a communication from the SICD or SCM to the LCP would occur to cause shortening of the pace-pace interval 674 prior to the next pace delivery at 680. On the other hand, if the morphology at 672 did not match the fusion morphology and instead resembled an LV pace-captured beat, then a communication from the SICD or SCM to the LCP would occur to cause an extension of the pace-pace interval 674 prior to the next pace delivery at 680.

In some examples, an analytical result for QRS complex 672 may not be ready in time to adjust interval 674. For example, the SICD or SCM may wait until completion of the QRS complex 672 before initiating analysis of it, making for some delay before a conclusion can be reached. Then, communication of the conclusion may add additional time lag. As a result, the interval following pace 680 may be modified in light of the QRS complex at 672, rather than interval 674 being adjusted. In other examples, analysis of QRS 672 may be performed to allow adjustment of interval 674, adjusting pace delivery at 680 to maintain fusion.

Figure 13:
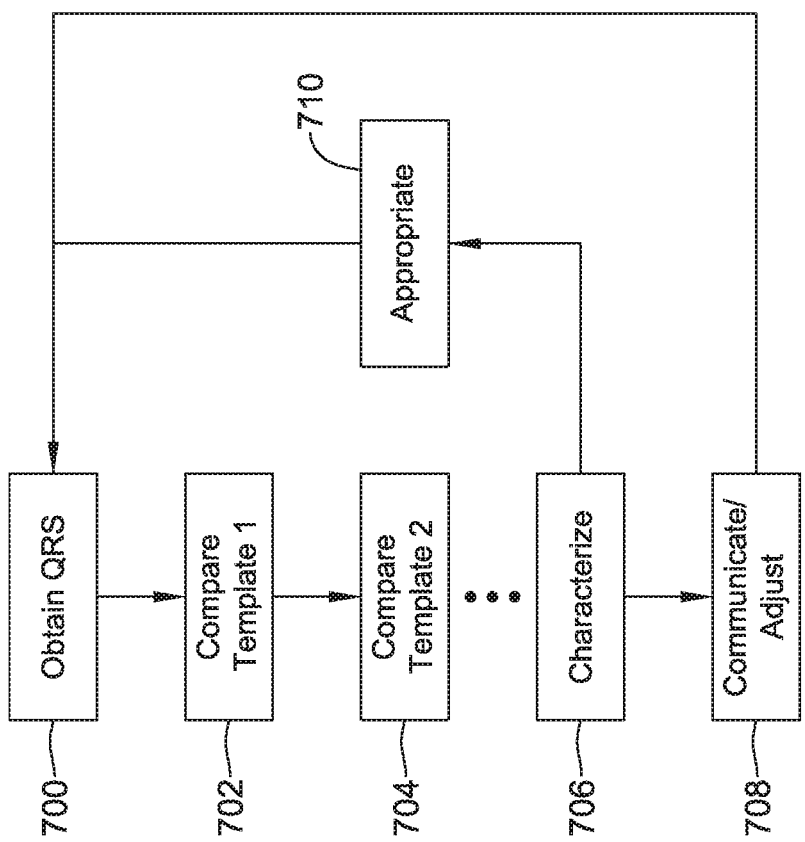
FIGS. 13 and 14 illustrate methods of promoting fusion pacing.
Figure 14:
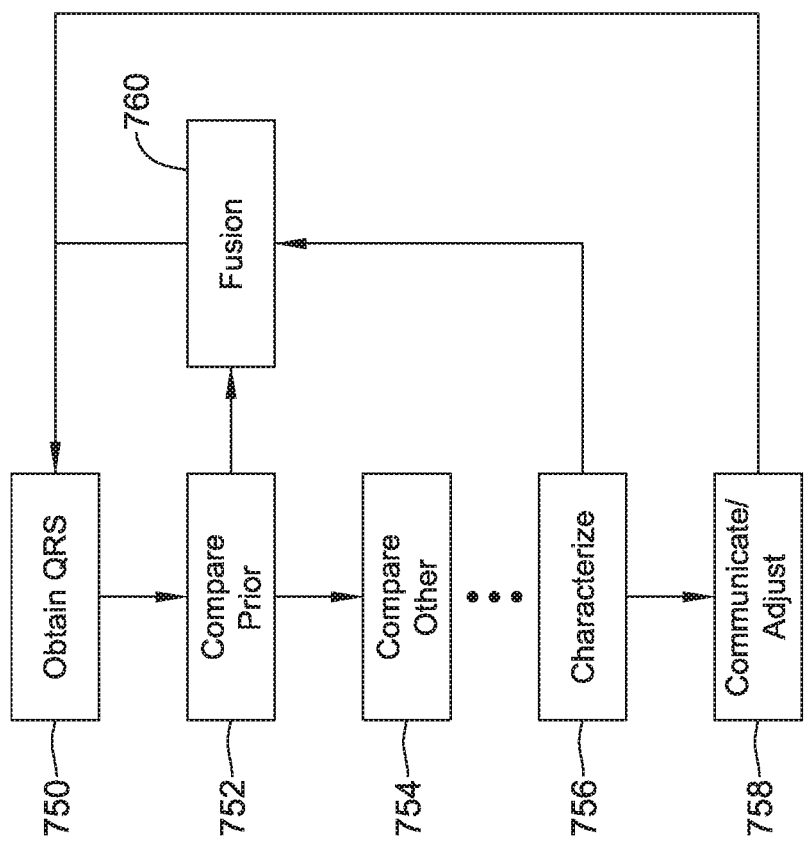

FIGS. 13 and 14 illustrate methods of promoting fusion pacing. In FIG. 13, a QRS complex is obtained at 700, following delivery of a pacing pulse. Next, the QRS complex is compared to one or more templates, as indicated at 702, 704. One, two, or up to five or more templates may be compared. The result of template comparison is a characterization at 706 of the result of the pacing therapy that preceded the obtained QRS. Characterization may include, for example, determining whether fusion occurs and, if fusion did not occur, the nature of what did occur, whether it was a beat that resembled an intrinsic beat or an LV pace captured beat, or something entirely different such as a beat that occurred due to an arrhythmia such as atrial fibrillation or ventricular tachycardia or fibrillation. If the characterization determines that fusion occurred, this may be deemed appropriate at 710, and the device then waits for the next QRS to be delivered. Alternatively, a communication may be made to indicate that fusion was observed, or that an adjustment is desired to achieve better fusion, as indicated at 708. The method illustrated in FIG. 13 may be performed entirely by an SICD or SCM, with the communication being directed to a second device such as an LCP.

FIG. 14 shows an alternative method. Here, a QRS complex is obtained as indicated at 750, and then compared to a prior QRS complex, as indicated at 752. In this example, the comparison to the prior QRS complex 752 may be limited to occurring only if fusion has already been identified for the prior QRS complex. If the obtained QRS complex does match the prior QRS complex, it is determined that fusion is occurring at 760, and the device returns to block 750 until a next QRS complex is obtained.

If the prior beat is not matched at 752 (or if the prior beat is known to have been a non-fusion beat), comparison may be made to one or more other templates, or analysis may be performed using one or more other factors, such as a set of rules as described above, as indicated at 754. Next, the obtained QRS complex is characterized as indicated at 756. If the obtained QRS complex is characterized as representing desirable fusion, the method may return to block 750. Alternatively, a communication may be made to indicate that fusion was observed, or that an adjustment is desired to achieve better fusion, as indicated at 758. The method illustrated in FIG. 14 may be performed entirely by an SICD or SCM, with the communication being directed to a second device such as an LCP.

Figure 15:
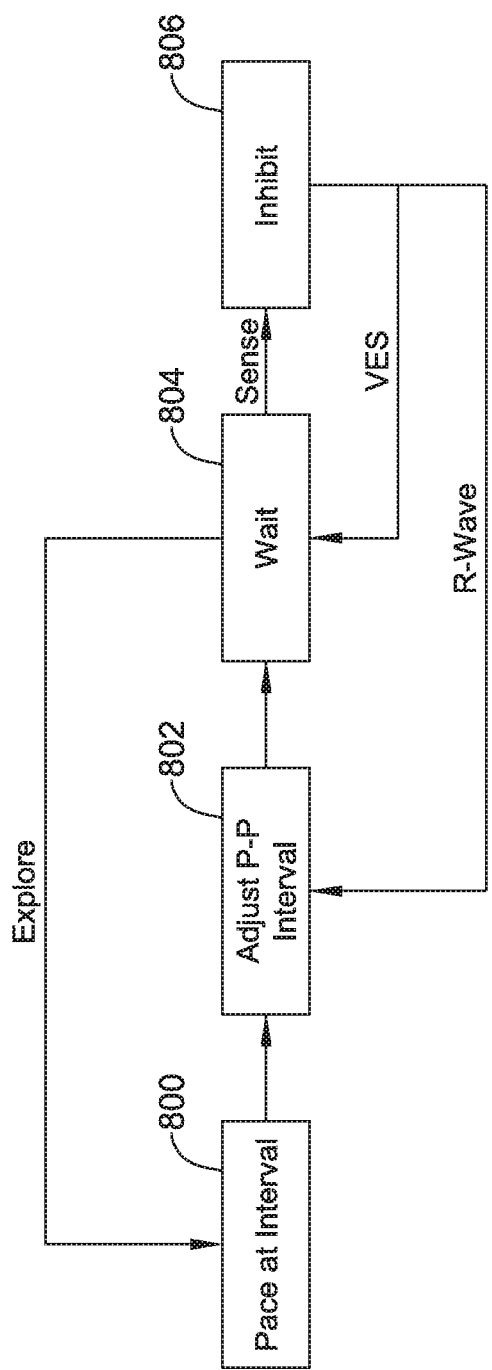
FIG. 15 illustrates a method of pacing with exception handling.

FIG. 15 illustrates a method of pacing using an exception handling routine. The device delivers a pacing therapy following expiration of an interval at 800. Next, the device may adjust the pace-to-pace (P-P) interval. For example, the pace-pace interval may be adjusted in response to a communication from a second device, such as an SICD or SCM, indicating that the result of pacing therapy (whether the one delivered at 800 or one or more prior therapy deliveries) was not the desired fusion. The second device may, for example, use a method as shown in FIG. 13 or FIG. 14, or in any other example discussed above.

Once the interval is adjusted at 802, the device waits for the adjusted interval to expire, as indicated at 804. In an alternative, an adjustment may be made to a subsequent pace-pace interval if, for example, the ongoing interval is already counting down. On expiration of the interval, the next pace is delivered with a return to block 800. While waiting for the interval to expire at 804, the device may actively sense for incoming cardiac signals or additional communications from one or more second devices. The detection of a cardiac signal or additional communication may be used to inhibit 806 the pacing therapy delivery 800. If, for example, a ventricular extra-systolic event (VES), such as a premature ventricular contraction (PVC), is found to have occurred, the device may return to the wait state at 804, but in this example restarts or doubles the interval in order to resume desired timing.

If a cardiac R-wave is detected, this may cause inhibition at 806 which sends the device back to block 802 to adjust the pace-pace interval. For example, as described above, the occurrence and identification of an intrinsic R-wave may cause the system to modify the pace-pace interval by shortening the interval. In addition, pacing parameters may also be adjusted to, for example, increase amplitude or pulsewidth, or to make other changes to polarity or waveform, as desired. The device would again enter the wait state at 804 and, on expiration, paces 800 at the new interval using, if adjusted, new pacing parameters.

The method of FIG. 15 can be performed entirely by an LCP, using communication with a second device such as an SICD or SCM in one or more of blocks 802, 806. In such examples, the LCP performs sensing during the wait state at 804 to detect any VES or other inhibitory event. In some alternatives, inhibition 806 may be caused if an SICD or SCM communicates with an LCP to indicate that an event has been identified that inhibits the pacing delivery. For example, the SICD or SCM may detect a VES and communicate to an LCP to request pacing inhibition. As noted, the second device such as an SICD or SCM may operate to assist with adjusting the pace-pace interval in block 802.

Figure 16:
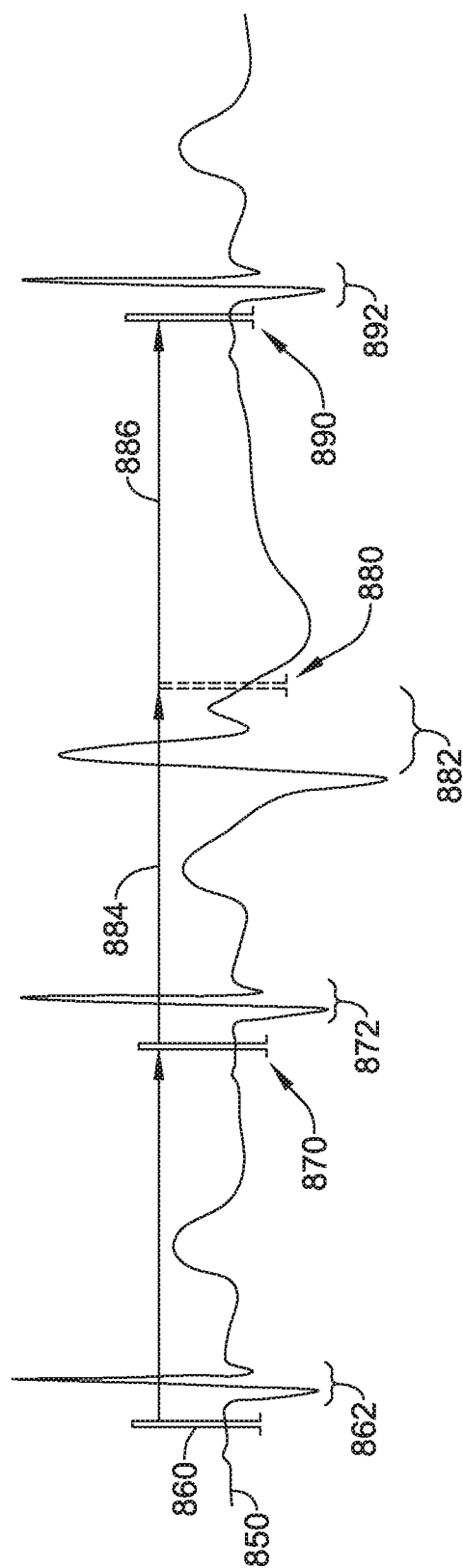
FIG. 16 illustrates an exception handling method

FIG. 16 illustrates an exception handling method. The cardiac signal as observed by an SCM or SICD is shown at 850. A first pacing pulse is delivered at 860, causing a fusion beat represented at QRS complex 862. A predetermined interval expires causing delivery of a next pacing pulse at 870, again causing a fusion beat represented at QRS complex 862.

A PVC occurs as shown at 880. The next pacing pulse at 882 is inhibited because the PVC took place prior to expiration of interval 884. There are several ways this may occur, including by the LCP sensing and detecting the PVC 880, or by an SICD or SCM detecting the PVC and communicating to the LCP. The PVC 880 is handled in this case by tacking on another interval 886 to interval 884, with new interval 886 being the same length as interval 884. Thus a next pace pulse is delivered at 890. In the example shown, the pace therapy 890 again causes a fusion beat 892.

A series of illustrative and non-limiting examples follows. These examples are provided for further illumination and is should be understood that other embodiments using other combinations of features are also contemplated.

A first illustrative non-limiting example takes the form of an implantable medical device (IMD) configured for use as part of a cardiac therapy system comprising a leadless cardiac pacemaker (LCP) and the IMD, the IMD comprising: a plurality of electrodes for sensing cardiac activity; communication circuitry for communicating with at least the LCP; operational circuitry configured to receive signals from the plurality of electrodes and analyze cardiac activity, the operational circuitry comprising: sensing means to sense QRS complexes; QRS complex analysis means to determine whether a selected QRS complex represents a fusion beat; and interval change means to cause the communication circuitry to communicate a pacing interval change to the LCP in order to promote fusion beats if the QRS complex does not represent a fusion beat.

An IMD as recited is shown in FIG. 1 at 16, and FIG. 2 at 50, and is further described in the above text associated with at least FIGS. 1-2. The inclusion of a plurality of electrodes is shown at least in FIG. 1 at 22, 24, 26 and 28 and again in FIG. 2 at 64, 66, and 72 and is further described in the above text associated with at least FIGS. 1-2. The inclusion of communication circuitry is shown for example at 62 of FIG. 2 and described in association therewith, including RF, inductive, and conducted communication, among other examples.

Operational circuitry is also illustrated at FIG. 2 as including, for example, various circuitry and memory associated therewith at 52, 54, 56, 58 and optionally 60. Sensing means may include means to sense a cardiac complex as indicated at 510 in FIG. 10, 610 in FIG. 11, at 700 in FIG. 13 and at 750 in FIG. 14, and may be operable by, for example, comparison of a sensed cardiac signal to a detection threshold as described above. The sensing means may include executable instructions stored in a memory for operation by a controller, or may include dedicated hardware to apply a detection threshold to an incoming data stream to generate, for example, an interrupt to a processor or to trigger other hardware to perform additional operations such as storing a quantity of signal likely to contain a QRS complex, for example.

QRS complex analysis means to determine whether a selected QRS complex represents a fusion beat may comprise executable instructions stored in a memory for operation by a controller to perform as illustrated, for example, at block 154 in FIG. 4, block 520 in FIG. 10, block 610 in FIG. 11, blocks 702, 704, 706 of FIG. 13, and blocks 752, 754, 756 of FIG. 14 and as described in text associated therewith. Alternatively the QRS complex analysis means may comprise dedicated hardware such as an application specific integrated chip or portion thereof to perform the steps illustrated, for example, at block 154 in FIG. 4, block 520 in FIG. 10, block 610 in FIG. 11, blocks 702, 704, 706 of FIG. 13, and blocks 752, 754, 756 of FIG. 14 and as described in text associated therewith.

Interval change means to cause the communication circuitry to communicate a pacing interval change to the LCP in order to promote fusion beats if the QRS complex does not represent a fusion beat may comprise executable instructions stored in a memory for operation by a controller to perform as illustrated, for example, at block 156 of FIG. 4, at block 530 of FIG. 10, block 630 of FIG. 1, block 708 of FIG. 13, and block 758 of FIG. 14, and as described in text associated therewith. Alternatively, the interval change means to cause the communication circuitry to communicate a pacing interval change to the LCP in order to promote fusion beats if the QRS complex does not represent a fusion beat may comprise dedicated hardware such as an application specific integrated chip or portion thereof to perform the steps illustrated, for example, at block 154 in FIG. 4, block 520 in FIG. 10, block 610 in FIG. 11, blocks 702, 704, 706 of FIG. 13, and blocks 752, 754, 756 of FIG. 14 and as described in text associated therewith.

A second illustrative non-limiting example takes the form of an IMD as in the first illustrative non-limiting example, wherein the QRS complex analysis means is configured to determine whether the selected QRS complex represents any of: a left ventricular (LV) paced beat, a fusion beat, or an intrinsic beat, wherein the interval change means is configured to communicate the following pacing interval changes based on the analysis of the QRS complex analysis means: if the QRS complex represents an LV paced beat, communicating an increase in the pacing interval is needed to the LCP; or if the QRS complex represents an intrinsic beat, communicating a decrease in the pacing interval is needed to the LCP.

A third illustrative non-limiting example takes the form of an IMD as in the first illustrative, non-limiting example, wherein the QRS complex analysis means is configured to determine whether the QRS complex represents a left ventricular (LV) paced beat or a fusion beat; wherein the interval change means is configured to communicate the following pacing interval changes based on the analysis of the QRS complex analysis means: if the QRS complex represents an LV paced beat, communicating an increase in the pacing interval is needed to the LCP; or otherwise communicating a decrease in the pacing interval is needed to the LCP.

A fourth illustrative non-limiting example takes the form of an IMD as in the first illustrative non-limiting example, wherein the QRS complex analysis means is configured to determine whether the QRS complex represents an intrinsic beat or a fusion beat; wherein the interval change means is configured to communicate the following pacing interval changes based on the analysis of the QRS complex analysis means: if the QRS complex represents an intrinsic beat, communicating a decrease in the pacing interval is needed to the LCP; or otherwise communicating an increase in the pacing interval is needed to the LCP.

A fifth illustrative non-limiting example takes the form of an IMD as any of the first to fourth illustrative non-limiting examples, wherein the operational circuitry comprises pace identification means to identify delivery of a pacing stimulus by the LCP and prompt analysis by the QRS complex analysis means in response to identifying delivery of the pacing stimulus. Pace identification means may take the form of executable instruction sets stored in a memory or dedicated hardware for performing a function configured to operate as described in association with block 512 in FIG. 10, and may make use of the input output circuitry 58 and processing block 52 as illustrated in FIG. 2.

A sixth illustrative non-limiting example takes the form of an IMD as in any of the first to fourth illustrative non-limiting examples, wherein the communications circuitry is configured to receive a communication from an LCP indicating delivery of a pacing stimulus by the LCP and prompt analysis by the QRS complex analysis means in response to receiving the communication from the LCP indicating delivery of the pacing stimulus.

A seventh illustrative non-limiting example takes the form of an IMD as in any of the first to sixth illustrative non-limiting examples wherein the QRS complex analysis means is configured to analyze the QRS complex to determine whether the QRS complex represents a fusion beat by comparing the QRS complex to a template for a fusion beat.

An eighth illustrative non-limiting example takes the form of an IMD as in any of the first to sixth illustrative non-limiting examples wherein the QRS complex analysis means is configured to analyze the QRS complex to determine whether the QRS complex represents a fusion beat by comparing the QRS complex to a plurality of templates including at least one template which represents a fusion beat and at least one template which does not represent a fusion beat.

A ninth illustrative non-limiting example takes the form of an IMD as in any of the first to sixth illustrative non-limiting examples, wherein the QRS complex analysis means is configured to use a combination of signal features to analyze the QRS complex to determine whether the QRS complex represents a fusion beat, including at least QRS width.

A tenth illustrative non-limiting example takes the form of an IMD as in any of the first to ninth illustrative non-limiting examples, wherein the QRS complex analysis means comprises composite signal means configured to combine the selected QRS complex with a plurality of other QRS complexes to generate a composite QRS complex, and wherein the QRS complex analysis means is configured to analyze the composite QRS complex to determine whether the selected QRS complex represents a fusion beat. The composite signal means may include executable instructions stored in a memory for operation by a controller, or may include dedicated hardware to generate a composite cardiac signal 410 from plural QRS complexes 402, 404, 406, as described above in association with FIG. 8.

An eleventh illustrative non-limiting example takes the form of an IMD as in the first illustrative, non-limiting example, wherein the QRS complex analysis means comprise current complex analysis means and prior complex analysis means, as follows: the prior complex analysis means is configured to compare the selected QRS complex to a preceding QRS complex, and if the QRS complex matches the preceding QRS complex and the preceding QRS complex represented a fusion beat, to determine that the selected QRS complex represents a fusion beat and otherwise to determine that the QRS complex does not represent a fusion beat; the current complex analysis means is configured to analyze the QRS complex by comparing it to at least one stored template including a template that represents a fusion beat; wherein the QRS complex analysis means is configured to determine whether the preceding QRS complex represented a fusion beat and: if so, to use the prior complex analysis means to determine whether the selected QRS complex represents a fusion beat; or if not, to use the current complex analysis means to determine whether the selected QRS complex represents a fusion beat. FIG. 10 illustrates that the QRS complex analysis means (block 520) may include prior complex analysis means indicated at 522, and a current complex analysis means using one or more templates as indicated at 524. As such, the current complex analysis means may include executable instructions stored in a memory for operation by a controller, or may include dedicated hardware to perform as indicated in block 524 and associated text, and the prior complex analysis means may include executable instructions stored in a memory for operation by a controller, or may include dedicated hardware to perform as indicated in block 522 and associated text.

A twelfth illustrative non-limiting example takes the form of an IMD as in the first illustrative, non-limiting example, wherein the QRS complex analysis means comprise current complex analysis means and prior complex analysis means, as follows: the prior complex analysis means is configured to compare the selected QRS complex to a preceding QRS complex, and if the QRS complex matches the preceding QRS complex and the preceding QRS complex represented a fusion beat, to determine that the selected QRS complex represents a fusion beat and otherwise to determine that the QRS complex does not represent a fusion beat; the current complex analysis means is configured to analyze the QRS complex by reviewing one or more rules including at least a first rule related to width and a second rule related to polarity; wherein the QRS complex analysis means is configured to determine whether the preceding QRS complex represented a fusion beat and: if so, to use the prior complex analysis means to determine whether the selected QRS complex represents a fusion beat; or if not, to use the current complex analysis means to determine whether the selected QRS complex represents a fusion beat. FIG. 10 illustrates that the QRS complex analysis means (block 520) may include prior complex analysis means indicated at 522, and a current complex analysis means using a set of rules as indicated at 526. As such, the current complex analysis means may include executable instructions stored in a memory for operation by a controller, or may include dedicated hardware to perform as indicated in block 526 and associated text, and the prior complex analysis means may include executable instructions stored in a memory for operation by a controller, or may include dedicated hardware to perform as indicated in block 522 and associated text. Text associated with block 526 illustrates that width, and other features noted in association with FIG. 9, may be used as such rules.

A thirteenth illustrative non-limiting example takes the form of an IMD as in any of the first to twelfth illustrative non-limiting examples, the IMD taking the form of an implantable cardiac monitor. A fourteenth illustrative non-limiting example takes the form of an IMD as in any of the first to twelfth illustrative non-limiting examples, the IMD taking the form of an implantable cardiac therapy device having therapy delivery circuitry configured to use at least first and second electrodes for delivery of therapy to the patient to address cardiac arrhythmia.

A fifteenth illustrative non-limiting example takes the form of a system comprising an IMD as in any of the first to fourteenth illustrative non-limiting examples, and further comprising an LCP, wherein the LCP is configured to receive a communication from the IMD indicating that a pacing interval change is needed to attain fusion and, in response to the communication, to make a change to a pace to pace interval.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable medical device (IMD) configured for use as part of a cardiac therapy system comprising a leadless cardiac pacemaker (LCP) and the IMD, the IMD comprising:
   a plurality of electrodes for sensing cardiac activity; and
   operational circuitry configured to receive signals from the plurality of electrodes and analyze cardiac activity as follows:
      sense a QRS complex; and
      analyze the QRS complex to determine whether the QRS complex represents a fusion beat;
   wherein the operational circuitry is further configured to communicate to the LCP that a pacing interval change is needed to attain fusion if the QRS complex does not represent a fusion beat;
   wherein the operational circuitry is configured to analyze the QRS complex to determine whether the QRS complex represents a fusion beat by comparing the QRS complex to a template for a fusion beat.

2. The IMD of claim 1 wherein the operational circuitry is configured to analyze the QRS complex to determine whether the QRS complex represents a left ventricular (LV) paced beat or an intrinsic beat and to determine whether the pacing interval change is an increase or decrease as follows:
   if the QRS complex represents an LV paced beat, determining that the pacing interval change is an increase in the pacing interval; or
   if the QRS complex represents an intrinsic beat, determining that the pacing interval change is a decrease in the pacing interval.

3. The IMD of claim 1 wherein the operational circuitry is configured to analyze the QRS complex to determine whether the QRS complex represents an intrinsic beat and to determine whether the pacing interval change is an increase or decrease as follows:
   if the QRS complex resembles an intrinsic beat, determining that the pacing interval change is a decrease in the pacing interval; or
   otherwise determining that the pacing interval change is an increase in the pacing interval.

4. The IMD of claim 1 wherein the operational circuitry is configured to form the template for a fusion beat by sensing one or more fusion beats and storing the fusion beat template.

5. The IMD of claim 1 wherein the operational circuitry is configured to analyze the QRS complex by comparing it to each of a fusion beat template and at least one of a pace captured beat template and an intrinsic beat template.

6. An IMD system comprising the IMD of claim 1 and a leadless cardiac pacemaker (LCP), the LCP comprising control circuitry adapted to perform each of issuing pacing pulses and at least receiving communication signals from the IMD and adjusting timing of pacing pulses in response to the IMD communicating that a pacing interval change is needed, and at least two electrodes for delivering the pacing pulses.

7. An implantable medical device (IMD) configured for use as part of a cardiac therapy system comprising a leadless cardiac pacemaker (LCP) and the IMD, the IMD comprising:
   a plurality of electrodes for sensing cardiac activity; and
   operational circuitry configured to receive signals from the plurality of electrodes and analyze cardiac activity as follows:
      sense a QRS complex; and
      analyze the QRS complex to determine whether the QRS complex represents a fusion beat;
   wherein the operational circuitry is further configured to communicate to the LCP that a pacing interval change is needed to attain fusion if the QRS complex does not represent a fusion beat;
   wherein the operational circuitry is configured to analyze the QRS complex to determine whether the QRS complex represents a left ventricular (LV) paced beat and to determine whether the pacing interval change is an increase or decrease as follows:
   if the QRS complex represents an LV paced beat, determining that the pacing interval change is an increase in the pacing interval; or
   otherwise determining that the pacing interval change is a decrease in the pacing interval.

8. An implantable medical device (IMD) configured for use as part of a cardiac therapy system comprising a leadless cardiac pacemaker (LCP) and the IMD, the IMD comprising:
   a plurality of electrodes for sensing cardiac activity; and
   operational circuitry configured to receive signals from the plurality of electrodes and monitor cardiac electrical signals to determine whether pacing therapy issued by the LCP is causing:
   a) one or more fusion beats;
   b) one or more pace captured beats; or
   c) one or more intrinsic beats; and
   selectively communicating to the LCP to adjust pace timing if the pacing therapy is not causing one or more fusion beats.

9. The IMD of claim 8 wherein the operational circuitry is configured to selectively communicate to the LCP to adjust pace timing as follows:
   if b), communicating an extension of the predetermined interval; and
   if c), communicating a reduction of the predetermined interval.

10. The IMD of claim 8 wherein the operational circuitry is configured to monitor the cardiac electrical signals by:
   obtaining a cardiac complex following a pace pulse delivery by the LCP; and
   compare the cardiac complex to a fusion beat template in order to determine which of a), b), or c) resulted from the pacing pulse.

11. The IMD of claim 8 wherein, if (c), the operational circuitry is configured to determine a time at which the pacing pulse was delivered by the LCP relative to the intrinsic beat and analyze whether:
   the pacing pulse was delivered too late to capture the heart of the patient and, to selectively communicate delivering the pacing pulse earlier for a subsequent cardiac cycle; or
   the pacing pulse was delivered at a time which likely cause a fusion beat and, if so, to selectively communicate an increase in at least one of pacing pulse amplitude or pacing pulse width for a subsequent pace pulse to be delivered by the LCP.

12. The IMD of claim 8 wherein the operational circuitry is configured to selectively communicate to the LCP after each detected cardiac beat.

13. The IMD of claim 8 wherein the operational circuitry is configured to selectively communicate to the LCP as follows:
   if a), communication is performed at an interval; or
   if b) or c), communication is performed to adjust the pacing parameters after each determination that b) or c) is taking place.

14. The IMD of claim 8 wherein the IMD does not separately detect an atrial event in order to analyze the cardiac electrical signal.

15. An implantable system comprising the IMD of claim 8 and a leadless cardiac pacemaker (LCP), the LCP comprising control circuitry adapted to perform each of issuing pacing pulses and at least receiving communication signals from the IMD and adjusting timing of pacing pulses in response to the IMD communicating that a pacing interval change is needed, and at least two electrodes for delivering the pacing pulses.

* * * * *